US010408733B2

(12) United States Patent
Kaye et al.

(10) Patent No.: US 10,408,733 B2
(45) Date of Patent: Sep. 10, 2019

(54) CRYSTALLINE PARTICLE DETECTION

(71) Applicant: Trolex Limited, Stockport (GB)

(72) Inventors: Paul Henry Kaye, Kimpton (GB); William Eugene Martin, Hemel Hempstead (GB)

(73) Assignee: Trolex Limited, Stockport (GB)

( * ) Notice: Subject to any disclaimer, the term of this patent is extended or adjusted under 35 U.S.C. 154(b) by 0 days.

(21) Appl. No.: 15/580,546

(22) PCT Filed: Jun. 8, 2016

(86) PCT No.: PCT/GB2016/051698
§ 371 (c)(1),
(2) Date: Dec. 7, 2017

(87) PCT Pub. No.: WO2016/198866
PCT Pub. Date: Dec. 15, 2016

(65) Prior Publication Data
US 2018/0231453 A1 Aug. 16, 2018

(30) Foreign Application Priority Data
Jun. 8, 2015 (GB) .................................. 1509926.0

(51) Int. Cl.
*G01N 15/14* (2006.01)
*G01N 15/00* (2006.01)
*G01N 21/21* (2006.01)

(52) U.S. Cl.
CPC ..... *G01N 15/1434* (2013.01); *G01N 15/1459* (2013.01); *G01N 2015/0046* (2013.01); *G01N 2021/216* (2013.01)

(58) Field of Classification Search
None
See application file for complete search history.

(56) References Cited

U.S. PATENT DOCUMENTS 3,901,602 A 8/1975 Gravatt, Jr.
7,378,861 B1 * 5/2008 Malendevich ......... G02B 6/124 324/750.23

(Continued)

FOREIGN PATENT DOCUMENTS

DE 102006030734 1/2008
GB 2311603 A 10/1997

(Continued)

OTHER PUBLICATIONS

International Search Report and Written Opinion for Application No. PCT/GB2016/051698 dated Sep. 20, 2016 (16 pages).

(Continued)

*Primary Examiner* — Shawn Decenzo
(74) *Attorney, Agent, or Firm* — Michael Best & Friedrich LLP

(57) ABSTRACT

A method for determining the presence of crystalline silica particles in a sample comprising a plurality of particles. The method comprises: receiving first data generated based upon light scattered by at least one particle of said plurality of particles; receiving second data generated based upon intensity and polarization change of the light transmitted through at least one particle of said plurality of particles; and determining the presence of crystalline silica particles in the sample based upon the first data and second data.

16 Claims, 16 Drawing Sheets

(56) References Cited

U.S. PATENT DOCUMENTS

2007/0058252 A1* 3/2007 Fritz .................. G01N 15/1404 359/485.05
2014/0036352 A1* 2/2014 Pronin .................. G02B 5/283 359/346

FOREIGN PATENT DOCUMENTS

GB 2333835 8/1999
GB 2456671 7/2009
GB 2511344 A 9/2014

OTHER PUBLICATIONS

United Kingdom Patent Office Action for Application No. GB1509926.0 dated Oct. 21, 2015 (3 pages).

Esswein, Eric J. et al., "Occupational Exposures to Respirable Crystalline Silica During Hydraulic Fracturing," Journal of Occupational and Environmental Hygiene, 10: 347-356, 2013.

Kaye, P.H. et al., P 2008, "Classifying atmospheric ice crystals by spatial light scattering," Optics Letters, vol. 33, No. 13, pp. 1545-1547.

Kaye, P.H. et al., "An Instrument for the Classification of Airborne Particles on the Basis of Size, Shape and Count Frequency," Atmospheric Environment, Part A, General Topics, Elsevier, vol. 25A, No. 3/04, Jan. 1, 1991, pp. 645-654.

Martin, W.E. et al., "Polarized optical scattering signatures from biological materials," Journal of Quantitative Spectroscopy and Radiative Transfer, Elsevier Science, Oxford, GB, vol. 111, No. 16, Nov. 1, 2010, pp. 244-2459.

Kaye, Paul H. et al., "Review Article; Spatial light-scattering analysis as a means of characterizing and classifying non-spherical particles," Measurement Science and Technology, IOP, Bristol, GB, vol. 9, No. 2, Feb. 1, 1998, pp. 141-149.

International Search Report for Application No. PCT/GB2016/051698 dated Sep. 20, 2016 (3 pages).

* cited by examiner

CRYSTALLINE PARTICLE DETECTION

RELATED APPLICATION DATA

This application is a U.S. national stage filing under 35 U.S.C. 371 of International Application No. PCT/GB2016/051698, filed Jun. 8, 2016, which application claims priority to Great Britain Patent Application No. 1509926.0, filed Jun. 8, 2015, each of which are incorporated herein by reference in their entireties.

TECHNICAL FIELD

The present invention relates to a method for determining whether a particle is a crystalline particle. More particularly, but not exclusively, the present invention relates to a method for determining whether a particle in an air sample is a Respirable Crystalline Silica RCS particle.

BACKGROUND

Crystalline particles such as RCS are a major occupational health and safety issue in industries such as mining, sandblasting, foundry work, agriculture, and construction. Minute shard-like particles of RCS (or other crystalline particles) can be carried in air currents for considerable distances and, if inhaled, are small enough to enter the deepest parts of the lung (alveoli) where they can become trapped. The resistance of crystalline particles to the body's attempts to remove them or chemically break them down means that they remain in the lungs for considerable periods, during which time they continue to cause irritation and damage.

Eric J. Esswein et al., (Eric J. Esswein, Michael Breitenstein, John Snawder, Max Kiefer and W. Karl Sieber, Journal of Occupational and Environmental Hygiene, 10: 347-356, 2013), describes a previously unreported occupational health hazard, that of worker exposure to RCS during hydraulic fracturing, or 'fracking', to extract shale gas and oil. Fracking operations have in recent times seen substantial and rapid expansion and have raised new concerns over the release of RCS into the atmosphere around fracking sites and the consequent potential for not only worker exposure but also, because of the proximity of many sites to residential areas, members of the general public.

Fracking involves high pressure injection of large volumes of water and sand, and smaller quantities of well treatment chemicals, into a gas or oil well to fracture shale or other rock formations, allowing more efficient recovery of hydrocarbons from a petroleum-bearing reservoir. Crystalline silica (quartz), also known as frac-sand, is a hard material commonly used in the operations to hold open cracks and fissures created by hydraulic pressure.

Each stage of the fracking process requires many tonnes of quartz-containing sand, and this may be repeated many times over the geographic extent of the reservoir. The generation of RCS may occur throughout the fracking process, from the initial delivery of the bulk fracking sand by road or rail, through to the mechanical unloading and storage of the fracking sand, and to the ultimate mixing of the sand with water and treatment chemicals. RCS is a significant health hazard if inhaled, and can cause health problems such as silicosis of the lungs and a variety of other life threatening conditions.

Current methods of monitoring the amount of RCS in the atmosphere rely on its collection through a fine-pore filter over a sampling period of hours or days. The filter is then carefully removed, packaged, and shipped to an external laboratory for gravimetric analysis and analysis via optical microscopy and/or X-ray crystallography analysis to determine the quantity of RCS that may be present. Knowledge of the volume of air that had been drawn through the filter then allows an estimate of the mass per unit volume of RCS that had been present in the vicinity of the filter unit over the course of the sampling.

However, this process has two significant disadvantages: Firstly, the time taken to collect, ship, and analyse the filter sample is typically days, during which time potential exposure of personnel is continuing. Secondly, the results from the filter simply reveal a total RCS mass estimate collected over the entire sampling period. The subsequently calculated mass per unit volume of air is therefore by necessity an average over the entire sampling period. This average may well hide so-called exceedances where the concentration of RCS in the air may, for short periods, be very much higher than safe limits of exposure.

SUMMARY OF THE INVENTION

In a first aspect of the invention there is provided a method for determining the presence of crystalline silica particles in a sample comprising a plurality of particles. The method comprises receiving first data generated based upon light scattered by at least one particle of said plurality of particles, receiving second data generated based upon light transmitted through at least one particle of said plurality of particles, and determining the presence of crystalline silica particles in the sample based upon the first data and second data.

Advantageously, aspects provide methods and apparatus for detecting crystalline particles, such as RCS or other particles having similar properties, in real-time that can operate continuously in the environment. By detecting levels of RCS in real-time, warnings of exceedance can be provided almost immediately allowing personnel to take protective measures such as putting on protective equipment or evacuating the work site.

Said first data may be based upon a relationship between light scattered by said at least one particle in first and second directions. The relationship may be based upon a difference between light scattered by said at least one particle in said first and second directions. The difference between light scattered by said at least one particle in said first and second directions may be a scatter ratio. For example, the scatter ratio may be a ratio of the amount of light scattered in the first direction to the amount of light scattered in the second direction.

Said first data may be based upon a first output of a first detector associated with said first direction and a second output of a second detector associated with said second direction. The association of first and second detectors with the first and second directions may be an association whereby light scattered in the first direction is detected by the first detector and light scattered in the second direction is detected by the second detector.

The light scattered in the first direction may be collected by a first collection mirror and the light scattered in the second direction may be collected by a second collection mirror. The first and second collection mirrors may be elliptical mirrors. The first collection mirror may be configured to receive light scattered in the first direction, and direct the received light scattered in the first direction to the first detector. The second collection mirror may be configured to receive light scattered in the second direction, and direct the received light scattered in the second direction to the second detector.

Said first detector may be arranged to detect light scattered by said particle on a first side of a plane defined based upon a source of said light and said particle and said second detector may be arranged to detect light scattered by said particle on a second side of said plane.

The method may further comprise, for each particle of said plurality of particles associated with said first data: determining whether said light scattered by said particle in first and second directions satisfies a predetermined criterion; and determining the presence of crystalline silica particles in the sample based upon light scattered by said particle if said predetermined criterion is satisfied. The predetermined criterion may be associated with a size of the particle. The predetermined criterion may be based upon a total light scattered in said first and second direction and may, for example, be based upon a sum of the outputs from first and second detectors associated with detection of light scattered in the first and second directions. Respective data values associated with scattering of light by a plurality of particles may be received and filtered to generate the first data. That is, the first data used to determine the presence of crystalline silica particles in the sample may therefore be based upon a subset of the particles for which scattering information is obtained.

The method may comprise receiving data for each of the plurality of particles associated with light scattered by the particle and associated with light transmitted through the particle. The received data associated with light scattered by the particle may be filtered to generate the first as described above.

The first data may be based upon third output of a third detector and data indicating a relationship between the third detector and the light source.

The relationship between the third detector and the light source may comprise a difference between a location associated with the third detector and a location associated with the light source. The locations may be locations of a reference plane associated with the third detector. The method may further comprise determining whether the difference exceeds a predetermined value. The relationship may be based upon a centroid of intensity of the light scattered by a particle and detected at the detector. Any suitable calculation may be used to determine the centroid of intensity of the light scattered by the particle.

The second data may be based upon a change in polarity of said light transmitted through said at least one particle.

The method may further comprise: emitting, from a light source, a light beam. The light source may be a laser and the light beam may be a laser beam. The light associated with generation of the first and second data may be generated based upon light emitted from said light source that is incident on the particle. The light emitted from the light source may be polarised light. The light transmitted through said at least one particle may be emitted from said light source. The polarized light beam may comprise circularly polarized light. The light may be either left or right hand polarised. The light may, for example, be polarised by passing light emitted from the light source through a filter configured to filter light not having a predetermined polarisation. The light transmitted through the at least one particle may be transmitted through a further polarising filter having the same polarisation as the light beam emitted from the light source. The light may have a wavelength in the range 500 nm to 540 nm, preferably 520 nm.

The first data may comprise respective data generated based upon light scattered by one or more of said plurality of particles. The second data may comprise respective data generated based upon light transmitted through one or more of said plurality of particles. That is, the first data and second data may comprise a plurality of values, each of the plurality of values being associated with a respective particle of the plurality of particles. The first data may comprise respective values associated with a first plurality of said plurality of particles, and the second data may comprise respective values associated with a second plurality of said plurality of particles. The first and second plurality may be associated with respective different subsets of the plurality of particles. It has been found that crystalline silica particles typically either generally scatter light or transmit light. As such, it has been found that by processing a plurality of particles and using both data indicative of scattering of light by a particle and data associated with birefringence of a particle for a set of particles provides good differentiation over other particles. It should, however, be noted that some particles provide both scattering of light and birefringence of light. As such, the first and second plurality may be associated with overlapping subsets of the plurality of particles.

The method may further comprise receiving first reference data associated with said at least one of said first and second data, wherein said determining is further based upon said first reference data. The method may further comprise determining a difference between said first reference data and said at least one of said first and second data associated with said first reference data. The first reference data may be based upon data generated from measurements of a background sample comprising a plurality of particles. In this way, variation of both scattering of light and birefringence of light relative to a known background may be used to determine the presence of particles such as crystalline silica particles. Using both scattering and birefringence of particles has been found to provide good differentiation over other particle types.

According to a second aspect there is provided a device for detecting the presence of a crystalline silica particle in a gas sample, the device comprising: a polarised light source arranged to emit a light beam having a first polarisation onto a particle of said gas sample; a detector arranged to detect light transmitted through said particle having a polarisation different to said first polarisation; and a processor arranged to determine the presence of a crystalline silica particle in the gas based upon output of said detector.

The polarised light source may comprise a light source and a first polariser arranged to polarise light emitted from said light source with said first polarisation. The device may further comprise a second polariser. The second polariser may be arranged such that light detected at said detector is transmitted through said second polariser. The second polariser may be arranged to prevent light having said first polarisation being transmitted to said detector.

Light transmitted through the particle to the detector may therefore first pass through the second polariser. If the light transmitted through the particle has the same polarisation as the light emitted from the polarised light source, light transmitted through the particle will not be detected at the detector. Conversely, light that has its polarisation modified when transmitted through the particle will pass through the second polariser and will be detected at the detector. The first polarisation may be a circular polarisation. The polarised light source may be arranged to emit a light beam having a wavelength in the range 500 nm to 540 nm, preferably 520 nm. It has been found that use of circularly polarised light having a wavelength of the order of 520 nm provides improved performance in detecting birefringence, with reduced noise over using lasers having greater wavelengths.

The processor may be arranged to process said output of said detector based upon a threshold. The processing of said output of said detector may be based upon a magnitude of said output of said detector. Alternatively, the processing may be based on an indication of detection of a particle, for example based upon an indication that a signal indicative of a birefringent particle being present in the device is received, for example a signal that exceeds a predetermined threshold is detected.

The processor may be arranged to receive output of said detector associated with a plurality of particles, wherein determining the presence of a crystalline silica particle in the gas is based upon said output of said detector associated with said plurality of particles. The processor may be arranged to determine a relationship between said output of said detector associated with said plurality of particles and reference data. The reference data may be based upon data generated from measurements of a background sample comprising a plurality of particles, for example a plurality of particles of a known type of having known properties. Alternatively, the background sample may be a sample obtained from an environment having a known property such as an environment in which the device is to be used prior to commencing an activity that may cause an increase in crystalline silica particles in the air.

The device may further comprise a further detector arranged to detect light scattered by the particle when the light beam is incident on the particle. The further detector may comprise a first detector arranged to detect light scattered by the particle in a first direction and a second detector arranged to detect light scattered by the particle in a second direction. The processor may be arranged to determine the presence of a crystalline silica particle in the gas based upon output of the further detector. The processor may be arranged to carry out a method according to the first aspect.

The device may further comprise an inlet; and a detection chamber. The detection chamber may be arranged to receive a particle in the gas sample whilst light is emitted onto the particle.

According to a third aspect there is provided a device for detecting the presence of a crystalline silica particle, the device comprising: a light source arranged to emit a light beam onto a particle; a first detector arranged to detect light transmitted through said particle; a second detector arranged to detect light scattered by said particle; and a processor arranged to determine the presence of a crystalline silica particle based upon output of said first detector and said second detector. The processor may be arranged to determine the presence of a crystalline silica particle based upon output of said first detector and said second detector associated with a plurality of particles. The third aspect may comprise one or more features of the second aspect, either alone or in combination.

According to a fourth aspect, there is provided a method for detecting a crystalline particle. The method comprises receiving first data, where the first data is based upon an output of a detector. The output is generated based upon light scattered by the particle and detected at the detector when a light beam emitted from a light source is incident on the particle. Second data is received which indicates a relationship between the detector and the light source. A determination is then made as to whether the particle is a crystalline particle based upon a relationship between the first data and the second data.

The relationship between the first data and the second data may comprise a difference between a location associated with the first data and a location associated with the second data. The locations may be locations of a reference plane associated with the detector. The step of determining whether the particle is a crystalline particle based upon a relationship between the first data and the second data may comprise determining whether the difference exceeds a predetermined value.

The first data may be associated with a centroid of intensity of the light scattered by the particle and detected at the detector. Any suitable calculation may be used to determine the centroid of intensity of the light scattered by the particle.

The second data may be based upon a relationship between an axis of the light beam emitted by the light source and a reference plane of the detector. The second data may comprise a location at which the axis of the light beam intersects the reference plane associated with the detector. The axis may be arranged so as to be normal to the plane of the reference plane. The reference plane of the detector may correspond with a surface of the detector, where the surface is arranged to detect the light scattered by the particle. The detector may comprise a planar surface which corresponds with the reference plane, and the planar surface be arranged to detect the light scattered by the particles. The surface may be a photosensitive surface of the detector, such as a PSD device, CMOS or CCD array. The position on the reference plane through which the axis of the light beam intersects may be arranged to coincide with a central region of the photosensitive surface of the detector. This may correspond with a central region of the reference plane.

The light source may be a laser and the light beam may be a laser beam.

The predetermined value may relate to a radial boundary having a centre corresponding to the position on the reference plane through which the axis of the light beam intersects. The radius of the radial boundary may be defined by a scattering angle of the light scattered by the particle being equal to or less than about 10 degrees. It will be appreciated that any suitable radius may be chosen for the particular circumstances relating to the environment that the device is intended to be used. A suitable radius may be found by performing field tests with the equipment in particular locations, or with particular sized RCS particles.

The method may further comprise emitting, from the light source, a light beam on to the particle, and detecting, by the detector, light scattered by the particle when the light beam is incident on the particle, where the first data is based upon output from the detector.

The method may further comprise receiving third data indicating fluorescence of the particle, where the step of determining that the particle is a crystalline particle is further based upon said fluorescence of the particle. This step may be achieved by comparing an intensity of fluorescence emitted by the particle with a value of intensity of fluorescence of a known crystalline particle. The third data may be generated based upon an ultra-violet light beam emitted by an ultra-violet light source. For example, the ultra-violet light beam may be incident on the particle, and a second detector may be arranged to detect fluorescent light emitted by the particle.

As some crystalline particles, including crystalline silica particles, are known to fluoresce, the step of determining measurements relating to the fluorescence of a particle and comparing this to known values of fluorescence of crystalline particles increases the confidence that a particle is a crystalline particle.

The method may further comprise receiving fourth data, indicating birefringence of the particle, where determining that the particle is a crystalline particle is further based upon said birefringence of the particle. The step of determining that the particle is a crystalline particle may comprise determining whether the particle is birefringent. The fourth data may be generated based upon polarisation of light incident on the particle. For example, polarised light may be incident on the particle and a third detector may be arranged to detect any change in the polarisation of the polarised light. For example, the detector may comprise a polarising filter having a polarisation at right angles to the polarisation of the incident polarised light beam, or be circularly polarised having an opposite handedness (i.e. :rotation) of the incident polarised light beam. If any light from the polarised light beam passes through the filter, it can be determined that the polarisation of the light was changed as it passed through the particle, indicating birefringence. As some crystalline particles, including crystalline silica particles, are known to be birefringent, detecting birefringence further increases the confidence that the particle is a crystalline particle.

The method may further comprise receiving fifth data, indicating a size of the particle and using the fifth data to determine whether the crystalline particle is a respirable crystalline particle. The fifth data may be based on measurements from the detector. Alternatively, the fifth data may be assumed to be within a particular range based upon conditions of the environment in which the detector is placed.

In a fifth aspect, there is provided a method of determining a concentration of crystalline particles in an air sample. The method comprises processing each of a plurality of particles in the air sample using a method according to the first aspect of the invention, and determining a concentration of crystalline particles in the air sample based upon said processing.

The method may further comprise determining whether the concentration of crystalline particles in the air sample exceeds a predetermined threshold value, and outputs a warning signal indicating that the crystalline particle concentration exceeds the threshold value if the crystalline particle concentration exceeds the threshold value.

The crystalline particle may be a Respirable Crystalline Silica particle.

The detector may be a position sensitive detector. For example, the detector may be a PSD device, CMOS or CCD array.

In a sixth aspect, there is provided a system for detecting a crystalline particle. The system comprises a detection apparatus comprising; a light source arranged to emit a light beam on to a particle; a detector arranged to detect light scattered by the particle when the light beam is incident on the particle; and a first processor arranged to generate first data based upon the light scattered by the particle. The system further comprises a computer apparatus comprising; a receiver arranged to receive said first data; a second receiver arranged to receive second data indicating a relationship between the detector and the light source; and a second processor arranged to determine whether said particle is a crystalline particle based upon a relationship between said first data and said second data.

It will be appreciated that aspects can be implemented in any convenient form. For example, aspects may be implemented by appropriate computer programs which may be carried on appropriate carrier media which may be tangible carrier media (e.g. disks) or intangible carrier media (e.g. communications signals). Aspects may also be implemented using suitable apparatus which may take the form of programmable computers running computer programs arranged to implement the invention. Aspects can be combined such that features described in the context of one aspect may be combined with features of another aspect.

DETAILED DESCRIPTION

Figure 1:
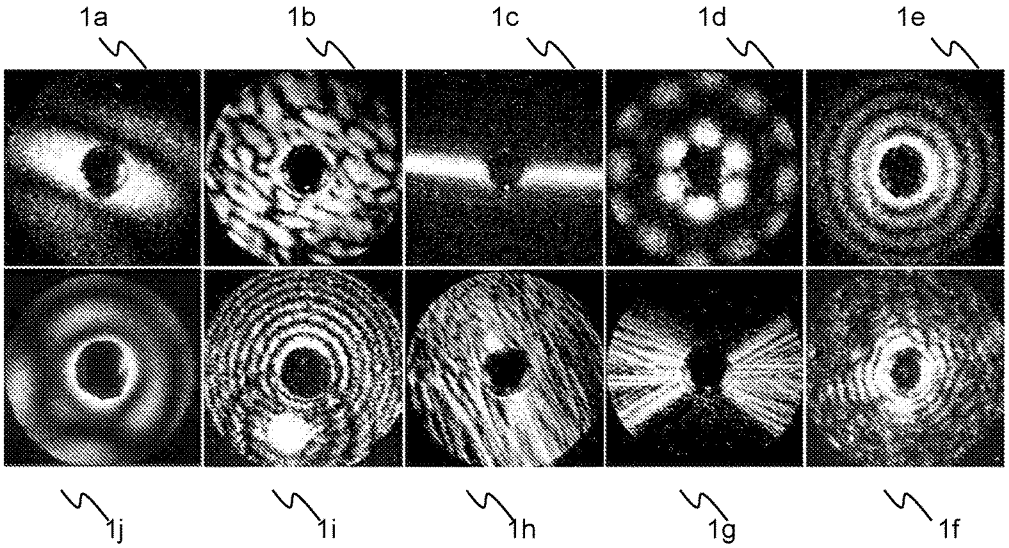
FIG. 1 illustrates scattering patterns of airborne particles.

In many fields of environmental monitoring, workplace monitoring, pollution control, and occupational health monitoring, it is necessary to continuously measure the airborne particle content of a local environment. Where real-time high-sensitivity measurements are desired, instruments are used that are capable of measuring the sizes of individual particles at high rates (typically thousands of particles per second) so that an accurate assessment of both the concentration of particles and their size distribution can be achieved. From these measurements, an estimate of particle mass concentration (mass per unit volume of air) can be determined. This is the parameter most frequently specified in statutory limits of exposure (LoE).

The instruments that are commonly used for this purpose are 'optical particle counters' (OPC). These use an intense light source (usually a laser) to illuminate a narrow column of sample air drawn through a sensing chamber by an electrical air-pump. The air column is sufficiently narrow that the volume of air illuminated by the laser beam—often referred to as the particle 'sensing zone'—rarely contains more than a single particle, and the pulse of light scattered by this particle as it crosses the laser beam is recorded as a particle count, the magnitude of the pulse being indicative of the particle size according to a calibration function. The calibration function depends on factors such as the laser wavelength, beam power and the solid angular range over which the scattered light from the particle is recorded. There are many commercial varieties of OPC manufactured by companies such as Met One Instruments (USA), Grimm Aerosol Technik GmbH (Germany), and Casella Measurement Ltd., (UK).

Each of these devices uses a mirror or lens assembly to capture the light scattered by each particle and focus it to a point on an optical detector such as a photodiode or photomultiplier tube. The solid angle over which the light is collected is usually as large as possible since this increases the signal magnitude from the optical detector and ultimately determines the size of the smallest detectable particles.

However, the distribution of light scattered in all directions by a particle, even one of symmetrical shape such as a sphere, is not uniform. Instead, this spatial distribution of scattered light is a complex function of the size, shape, and orientation of the particle being illuminated. Kaye P. H., Measurement Science and Technology, 9 (2), pp. 141-149, 1998 showed that characteristics of the distribution of scattered light—the so-called spatial light scattering pattern—can be used to classify or even identify particles of a given type, by comparing the scattering pattern with known patterns. For example, this approach has been used in the past as part of the detection procedure for hazardous airborne fibres such as asbestos (GB2333835B, Improved Method and Apparatus for Detection of Asbestos Fibres, 2002) or the detection of airborne biological organisms (GB2456671B, Fluid Borne Particle Detector, 2012).

FIG. 1 illustrates the type of scattering patterns that can be recorded from individual airborne particles, all less than 10 μm in size, illuminated by a laser beam. These patterns were recorded by an instrument that uses a very sensitive intensified camera (see for example: Kaye, P H, Hirst, E, Greenaway, R, Ulanowski, Z, Hesse, E, DeMott, P, Saunders, C & Connolly, P 2008, 'Classifying atmospheric ice crystals by spatial light scattering' Optics Letters, vol 33, no. 13, pp. 1545-1547, 10.1364/OL.33.001545).

In each case, the beam axis is directed towards the centre of each image, intersecting the dark disc at the centre of each pattern. The pattern therefore shows the distribution of light scattered by the particle around the laser beam (called azimuthal scattering) up to a scattering angle (the angle between the beam axis and the scattered ray) of approximately 25 degrees. The scattering pattern examples shown in FIG. 1 correspond to (clockwise from top-left)—an ellipsoidal particle 1*a*, a rough mineral dust particle 1*b*, a fibre particle 1*c* (in this case, blue asbestos), a cuboidal salt particle 1*d* (corner-on), a water droplet 1*e*, a near spherical pollen particle 1*f*, a curved fibre 1*g* (in this case, white asbestos), a large gypsum particle 1*h*, a droplet containing a solid inclusion 1*i*, and a fungal spore particle 1*j*.

Figure 2:
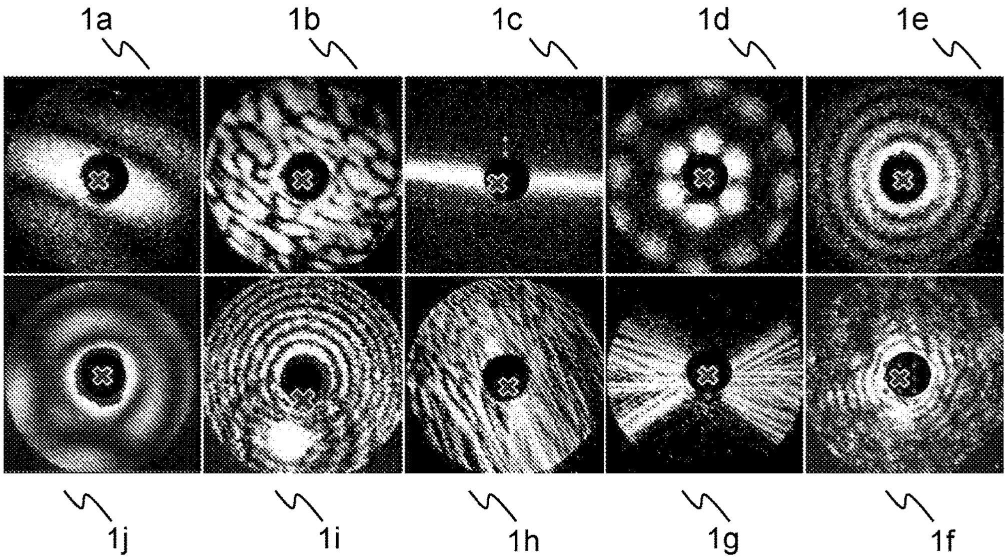
FIG. 2 illustrates centroid of intensities on each of the scattering patterns of FIG. 1.

Although the form of these patterns is very different for different particle types, the centroid of the light distribution within the pattern (akin to the centre of gravity of an object), is almost always close to the centre of the image, which corresponds with the point at which the axis of the laser beam intersects the image. In other words, regardless of the light pattern distribution, and therefore the type of particle producing it, the centroid of intensity of that pattern is closely aligned with point at which the axis of the laser beam intersects the image. FIG. 2 illustrates this by the addition of a cross in each image to mark the centroid of intensity.

Figure 3:
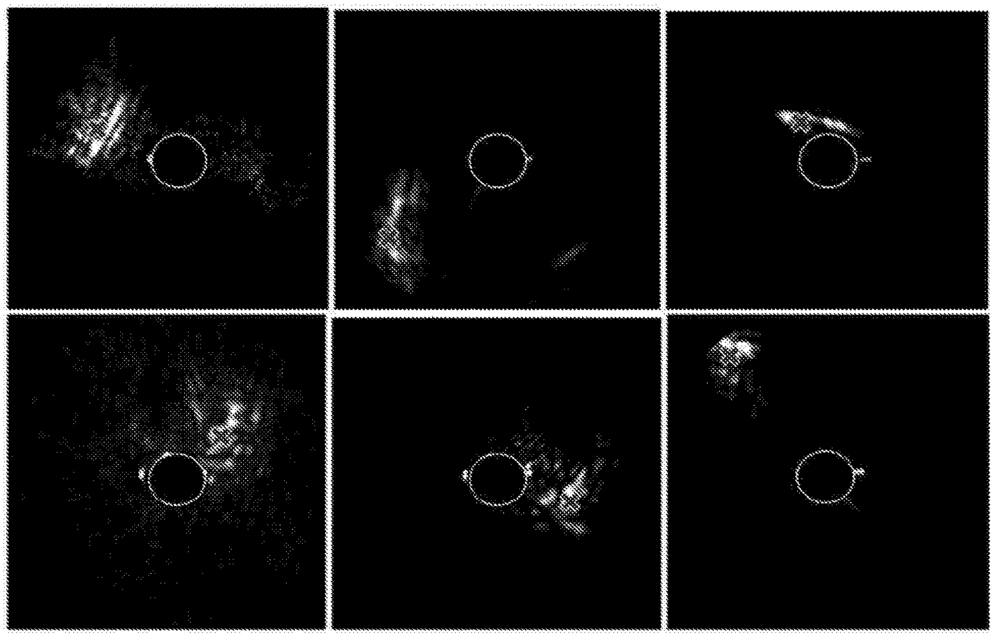
FIG. 3 illustrates scattering patterns of RCS.

The present invention is based upon the realisation that a relationship between the light beam used to generate light scattering patterns from crystalline particles, such as RCS, may be used to classify particles as crystalline particles. FIG. 3 shows examples of such patterns recorded from an aerosol of silica dust produced from crystalline sand used in 'fracking' operations. In a significant proportion of these patterns, the light distribution is localised to one small area of the image, away from the central region of the image (indicated by a white circle and which corresponds to a point at which the beam axis intersects the plane of the image). The corresponding centroid of intensity of the light patterns, indicated by a cross, is also a significant distance from the central region of the image. Hereafter, the term "image centre" is defined as "a point at which an illuminating light beam axis intersects the plane of the image." Therefore, the image centre as defined above need not be located at the physical centre of a scattering image. For example, if the laser axis is offset from the centre of an image plane of a light recording device, the resulting image will have an image centre offset from the physical centre of the image.

The position at which the beam axis intersects the plane of the image may be determined by any suitable means. For example, the position at which the beam axis intersects the plane of the image may be calibrated such that it corresponds with the centre of an image obtained from the light recording device. Alternatively, the position at which the beam axis intersects the plane of the image may be measured and recorded such that it may then mapped onto an image obtained from the light recording device.

Figure 4:
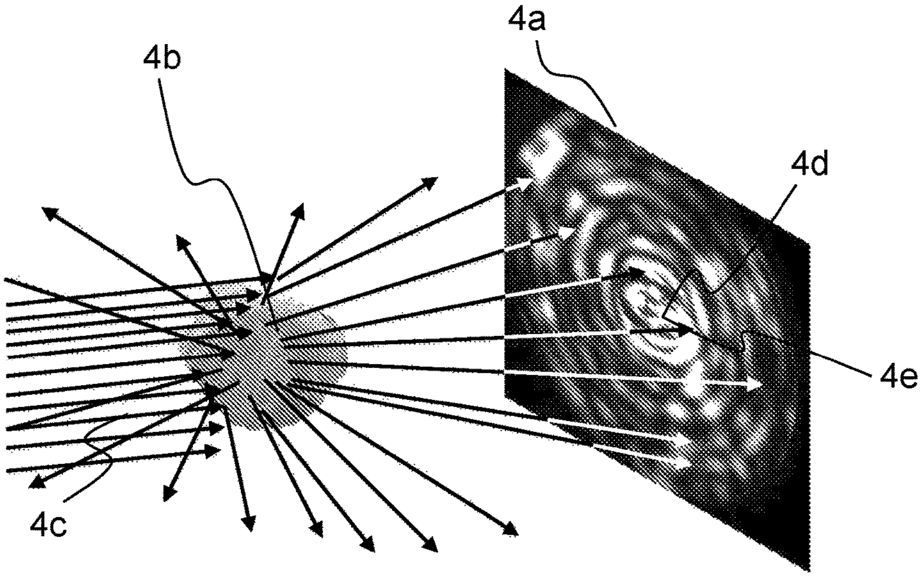
FIG. 4 schematically illustrates light being scattered by a common mineral dust particle.
Figure 5:
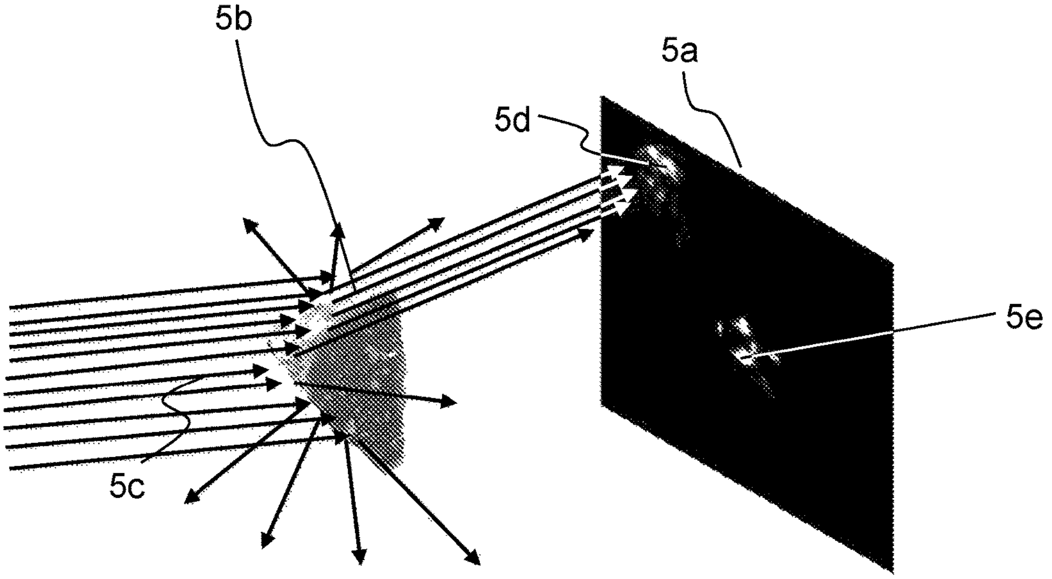
FIG. 5 schematically illustrates light being scattered by an RCS particle.

The origin of this behaviour is illustrated in FIGS. 4 and 5. FIG. 4 shows schematically the formation of a light scattering pattern 4*a* from a common mineral dust particle 4*b* illumined by a light beam 4*c*. The interaction of the light beam 4*c* with the particle 4*b* (here shown greatly enlarged in scale) is based in diffraction of rays around the particle 4*b* and (if the particle is partially transparent) the transmission and refraction of rays through the particle 4*b*. This results in a complex but overall fairly uniform intensity distribution having its centroid of intensity 4*d* at the centre of the pattern 4*e*.

FIG. 5 shows schematically the behaviour of a light beam interacting with a crystalline particle, such as RCS 5*b*. Such particles generally have facets as a result of fractures following crystal planes, and if such a facet is at an appropriate angle to the incident light, so called 'specular reflection' will occur from the facet, resulting in a localised patch of light 5*d* falling on the image plane 5*a*.

Figure 6:
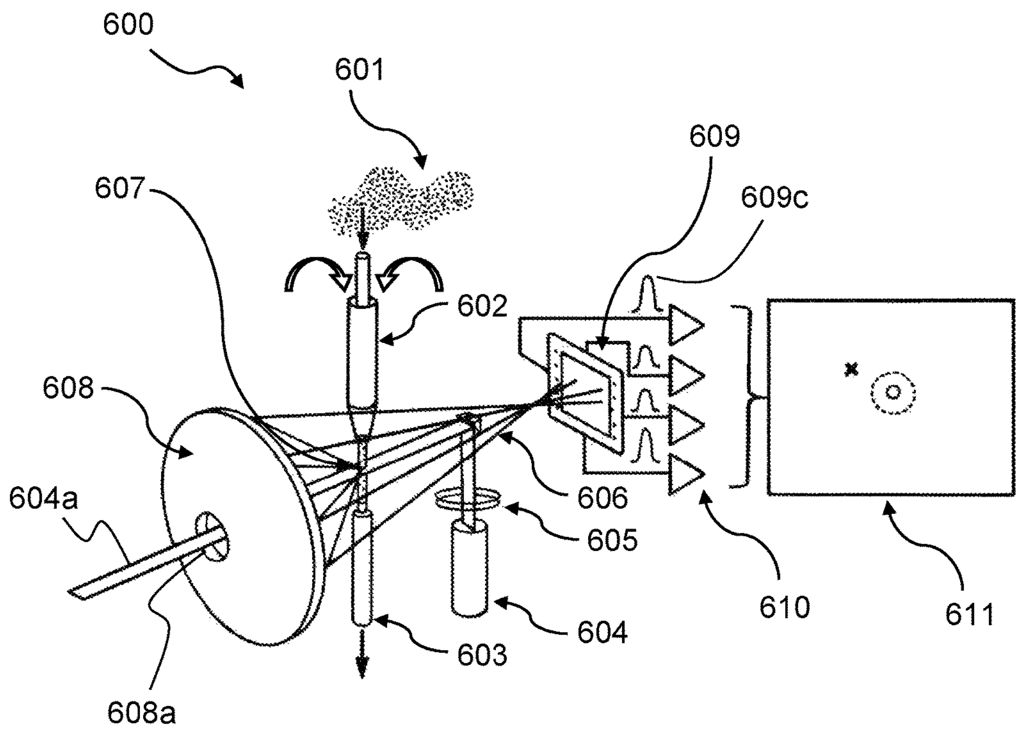
FIG. 6 schematically illustrates a sampling and detection apparatus.

Since the occurrence of such facetted crystalline particles is generally rare in ambient outdoor aerosols comprising mineral dust particles, pollens, fungal spores, combustion products, etc., measurement of the relative positioning of the pattern centroid of intensity 5*d* can provide a potential means of discriminating such crystalline particles from the remaining background ambient aerosol. More specifically, by determining the position of the centroid of intensity 5*d* relative to the image centre 5*e*, it can be determined whether the particle is likely to be a crystalline particle, such as RCS, or not FIG. 6 shows a schematic diagram of an apparatus 600 for detecting crystalline particles, such as RCS. Ambient airborne particles 601, which may or may not contain crystalline particles, are drawn by an air pump (not shown) into the apparatus 600 through a sample delivery tube 602. The air pump may be replaced by any suitable means that allows air to move through the apparatus 600, such as a fan. To ensure the particles in the 'sample flow' are constrained when passing through the apparatus 600, a so-called 'sheath-flow'(not shown) of filtered clean air may be added to surround the particle flow. A sheath flow helps to prevent particles at the edges of the flow being drawn out of the flow and into the chamber where they can contaminate, and over time, degrade the optical surfaces. The combined sample flow and sheath flow leave the instrument through a vent tube 603. The combined sample and sheath flows may be aerodynamically configured to ensure that particles 601 contained within the sample flow are essentially travelling in single file in the direction of flow. The skilled person will of course recognise that there are other ways to configure the sample flow such that the particles 601 contained within the sample flow travel in single file, where some of these ways do not require a sheath flow.

A diode laser module 604, comprising a diode laser and a collimating lens (not shown), produces a parallel beam of light which is typically elliptical in cross-section. In a preferred embodiment, the diode laser produces a laser having a wavelength of about 660 nm. This beam passes through a cylindrical lens 605 before being rotated through 90 degrees by a mirror 606. Any other means capable of rotating the beam, such as a prism, may be used. The lens 605 renders the beam into a thin ribbon shape, which, in some embodiments, has a cross section of typically 3 mm by 0.05 mm at the focus which is coincident with the cylindrical sample flow of airborne particles 601. The intersection of the laser beam and sample airflow defines a so-called 'sensing volume' 607. The laser beam has a main axis 604*a*, along which the beam is incident on the cylindrical sample flow of airborne particles 601.

In some embodiments the apparatus 600 may be arranged such that the probability of more than one particle being present in the sensing volume 607 at the same time is very low (typically less than 1%). Because the apparatus 600 relies on the measurement of the light scattering properties of a single particle to ascertain that particle's shape; if two or more particles are illuminated simultaneously, referred to as coincidence, such shape determination may become ambiguous. The dimensions of the sensing volume 607 therefore may be arranged to set a limit of the maximum concentration of airborne particles that can be measured without excessive coincidence occurring. In a preferred embodiment, the design of the apparatus 600, in terms of sample flow column diameter and a beam depth at the sensing volume 607, is such that the maximum measurable particle concentration (corresponding to 1% coincidence losses) is of the order of about 1,000 particles/ml.

Each particle passing through the sensing volume 607 may scatter light in all directions. Light scattered in the forward direction, so-called 'forward scattering', strikes a concave elliptical mirror 608 whose first focus is at the centre of the sensing volume 607. An aperture 608*a* at the centre of the mirror 608 allows the passage of the unscattered laser beam which is subsequently terminated in a light absorbing material. The reflected light from the mirror 608 converges at a second focus of the elliptical mirror 608 before diverging to fall on an optical detector 609. The optical detector 609 shown in FIG. 6 is a Position Sensitive Detector or PSD (described in more detail below) and is connected to a simple electrical circuit 610 comprising operational amplifiers. However, the skilled person will recognise that any suitable optical detector may be used. The detector 609 outputs a signal 609*c* indicating positions at which light is detected on the detector 609. The signal 609*c* can then be processed to determine if the sample 601 contains crystalline particles, such as RSC, as described below. Information generated by processing the signal 609*c* can be presented to a user in the form of an audio warning, and/or a digital image 611, alerting the user to the presence of respirable crystalline particles, such as RCS.

Note that various modifications may be made to the apparatus 600 without departing from the invention. For example, the direction of the laser beam may be reversed so that the beam passes through the aperture 608*a* in the mirror 608 before reaching the sensing volume 607. Scattered light may then be collected by the mirror 608 and focused on the detector 609. The light scattering recorded by the apparatus in this arrangement is referred to as 'back scattered' light since it travels from the particles in the opposite direction to that of the illuminating laser beam.

As described above and illustrated in FIG. 2, the centroids of intensity of the scattering patterns from ambient airborne particles are typically close to the image centre. However, as illustrated in FIG. 3, the centroids of intensity of light scattering patterns from crystalline particles (where scattering from facets dominates) are typically much further away from the image centre. Thus, differentiation of a crystalline particle from other non-crystalline particles that pass through the apparatus 600 can be achieved by setting a radial boundary around the image centre. As defined above, the image centre corresponds to a point at which an illuminating light beam axis intersects the plane of the image. Therefore, a radial boundary around the image centre may be defined by a particular scattering angle. In some embodiments, the radial boundary may be selected such that light scattered with a scattering angle equal to or greater than 10 degrees will fall outside the radial boundary, and light scattered with a scattering angle less than 10 degrees will fall on or within the boundary. Therefore, particles whose scattering results in a centroid of intensity within the radial boundary are deemed likely to be non-crystalline, whereas particles whose scattering results in a centroid of intensity outside the radial boundary are deemed likely to be crystalline.

This process of differentiation is probabilistic since there is a small but finite probability of a crystalline particle producing a scattering centroid of intensity inside the boundary (see for example the cubic salt crystal example in FIG. 2 which, by chance, is corner-on to the illumination beam of light and which therefore produces a scattering pattern with radial symmetry for which the centroid of intensity would be close to the centre of the image.). Similarly, a non-crystalline particle may occasionally produce a centroid of intensity outside the boundary. Laboratory and field testing of the apparatus would allow empirical determination of the position of the boundary for a given confidence level, typically 95%.

Figure 7:
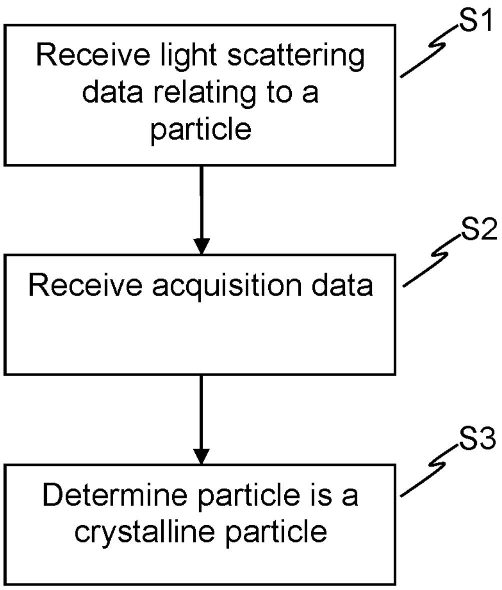
FIG. 7 is a flow chart describing a method for detecting crystalline particles.

FIG. 7 shows steps according to an embodiment of the invention.

At step S1 data captured by a detector is received. The data relates to scattered light from a light beam incident on a particle. This data may be captured using a sampling and detection apparatus comprising a detector, such as the apparatus 600 described above or apparatus 700 described below. For example, a laser beam may be directed onto a particle, and a portion of the light that is scattered off the particle may be collected by the detector. The data may relate to positions and intensities of the scattered light incident on a reference plane. The reference plane may correspond with a surface of the detector which is arranged to receive the scattered light. The data may relate to an angle of scattering of the scattered light.

The particle may be moving while the laser beam is directed onto the particle. For example, as described above, the particle may be travelling along a path in a sample flow.

At step S2, acquisition data is received. The acquisition data may relate to a relationship between the light beam and the detector. For example, the acquisition data may relate to the direction and/or orientation of the light beam relative to the sample and/or detector. For example, the acquisition data may specify a point at which the light beam axis intersects the reference plane on which the scattered light lands.

The acquisition data may be provided by the detector or apparatus, by a user, or may be inherently known. For example, if the apparatus is arranged such that the position at which the axis of the light beam intersects the reference plane coincides with a substantially central point of the reference plane, the acquisition data need not be sent, but can be assumed.

At step S3 a determination is made that the particle is a crystalline particle by determining a relationship between the data relating to scattered light and the acquisition data.

The relationship between the data relating to scattered light and the acquisition data may be a relationship between the relative positions on the reference plane of the scattered light and a position on the reference plane at which the axis of the light beam intersects the reference plane. For example, the relationship may relate to a distance or offset on the reference plane between a position at which the scattered light intersects the reference plane and a position on the reference plane at which the axis of the light beam intersects the reference plane. The position at which the axis of the light beam intersects the reference plane may be arranged to coincide with a substantially central point of the reference plane.

The concentration of crystalline particles in the air sample may be determined. For example, the number of particles per unit volume may be determined by dividing the number of detected crystalline particles detected per unit time by the volume of the air sample being passed through the sampling and detection apparatus per unit time. The mass concentration may also be determined by determining the size of the particles according to light scattering theory, and combining this information with information relating to the average density of the crystalline particles. Further data may be received relating to the volume of the air sample. This may be information relating to the volume of air containing crystalline particles that is passed through the sampling and detection apparatus per unit time. The determined concentration of crystalline particles may be compared with a threshold value. The threshold value may be a statutory limit of exposure to RCS.

If it is determined whether the crystalline particle concentration exceeds the threshold value, a warning signal may be output that indicates that the crystalline particle concentration exceeds the threshold value. The warning signal may, for example, be in the form of an audio or visual warning to personnel at a work site where the sampling is taking place. The warning signal may be sent to a plant or site wide monitoring or control system arranged to process the signal and generate output data.

If the crystalline particle concentration does not exceed the threshold value, the processing of FIG. 7 may be continually performed. In this way, continual, real-time monitoring of the air around a work site using crystalline particles may be achieved.

In order to improve the confidence of detection of a crystalline particle, further particle measurements may be made. For example, in addition to data relating to scattering of a light beam incident on a particle, further data relating to the birefringence of the particle may be received. Some crystalline particles, including RCS, are birefringent and therefore detection of birefringence in a particle deemed likely to be crystalline from the aforementioned light scattering test is a further indication that the particle is a crystalline particle, such as a crystalline silica particle. Other crystalline particles that may be found in the environment, such as sodium chloride crystals, are not birefringent, for example.

In order to detect birefringence, the particle may be illuminated with linearly polarised light and a birefringent detector may be used which has a filter having a polarisation at right angles to the incident polarised light. If the particle is not birefringent, the polarisation of light transmitted through the particle will not be rotated and thus will not pass through the filter. However, if the particle is birefringent, a portion of the polarised light will be rotated as it passes through the particle. This portion of light will then be able to pass through the polarisation filter and be recorded by the birefringent detector. Therefore, any observations of light being received at the detector indicate that the particle is birefringent. The level of birefringence may be determined based on the amount of light that is transmitted through the filter. Other methods may be used to detect birefringence. Instead of using linearly polarised illumination onto the particle, circularly polarised illumination can be used. In that case, the polarising filter receiving light transmitted through the particle would be circularly polarised also, but with the opposite handedness (i.e.: rotation).

Alternatively, or additionally, data relating to the particle's fluorescence may be received. This data may be obtained by illuminating the particle with ultra-violet light and using a detector to measure the fluorescence of the particle. Any measured fluorescence may then be compared with known values of crystalline particle fluorescence.

In some embodiments, the measurements described above may be combined to give a higher probability of determining that a particle is a crystalline silica particle as opposed to a crystalline non-silica particle. For example, if a particle gives a scattering pattern for which the centroid of intensity is more than 10 degrees from the centre of the image plane and the particle is found to be birefringent, and/or have a matching intrinsic fluorescence to a known crystalline silica particle, then it is more probable that the particle is a crystalline silica particle.

Thus, for each particle passing through the sensing volume 607 of FIG. 6 (at rates potentially reaching several thousand particles per second), a determination may be made of the shape of the particle (via the scattering pattern) and the crystalline properties of the particle (via the presence of birefringence and fluorescence). Furthermore, the size of the particle may also be determined based on the scattered light according to light scattering theory. Any of these parameters may be used, either on their own or in any combination, to assess the presence and concentration of crystalline particles within an air sample. Once crystalline particles are detected, an estimate of particle mass concentration may be made and compared with statutory limits of exposure. If the particle mass concentration of the crystalline particles exceeds safe levels, personal in the area may be warned. The particle mass concentration may be calculated by aggregating the number of particles deemed to be crystalline particles over a finite measurement period, such as 1 minute. The size of the crystalline particles may be determined according to light scattering theory, and by assuming a density of the crystalline particles (crystalline silica has a density of typically 2.65 g/cc, for example), the total mass of crystalline particles contained in the volume of air sample passing through the detector in the 1 minute period can be determined. Combining this information with information relating to the volume of air that has been sampled in the 1 minute period leads to a determination of the mass concentration of the crystalline particles.

Figure 8:
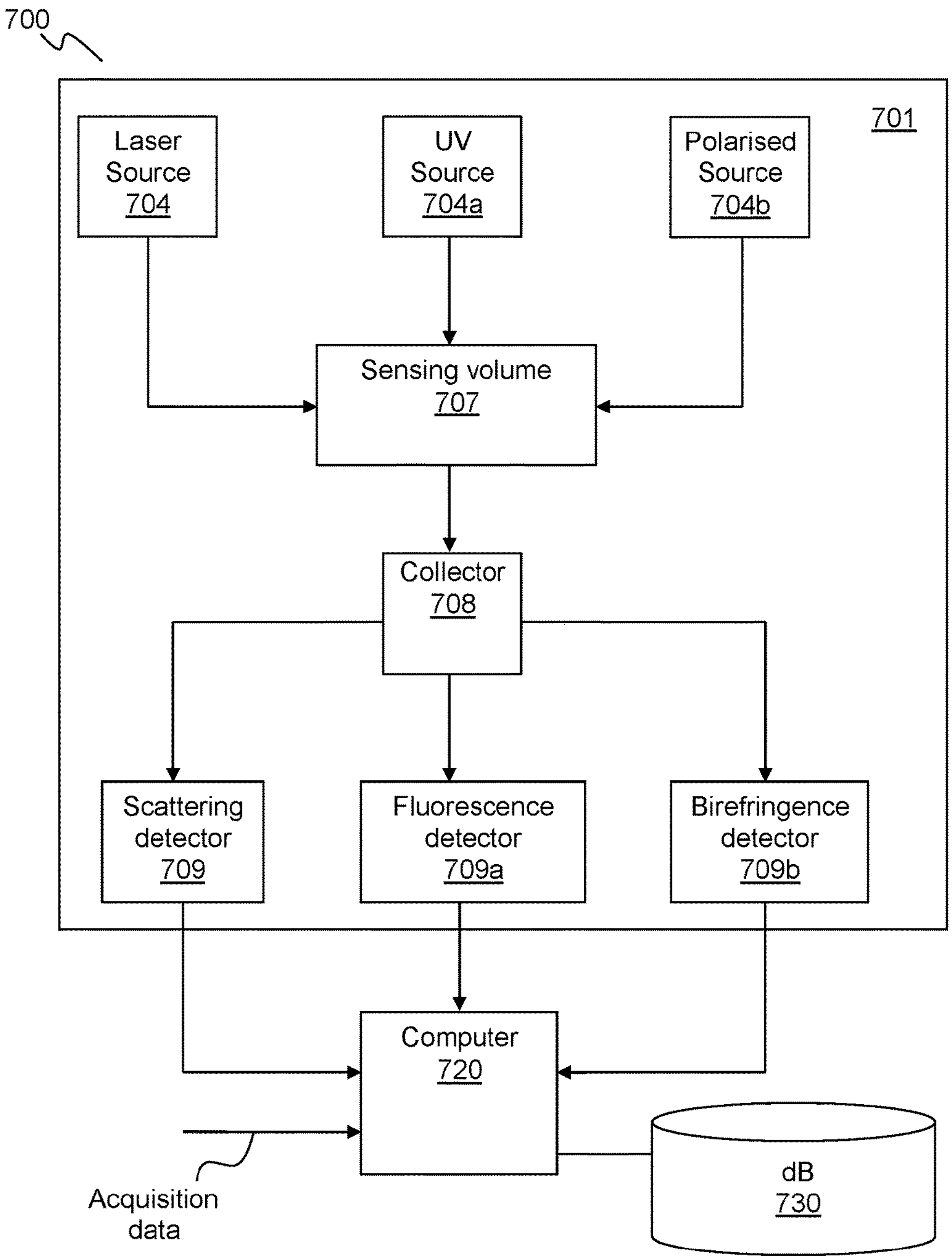
FIG. 8 schematically illustrates a further sampling and detection apparatus.

Referring to FIG. 8, a high level schematic diagram is shown of an apparatus 700 according to an embodiment of the invention. The apparatus 700 comprises a sampling module 701. The sampling module 701 may be similar to the apparatus 600 described above and like reference numerals have been used where appropriate. The sampling module 701 comprises a laser light source 704, and optionally an ultra-violet light source 704*a* and a polarised light source 704*b*. Note that the polarisation light source 704*b* may be replaced with a suitable polarising element used in conjunction with the ultra-violet light source 704*a*, for example. The light sources are arranged to provide light beams which are directed onto the sample airflow at the sensing volume 707. The light sources may be arranged to simultaneously illuminate the same particle or may be arranged to illuminate the particle in a sequential order as it travels through the module 701. A collector 708, such as a mirror, collects light that has been scattered, reflected, or refracted by a particle in the sensing volume 707, and directs it towards an appropriate detector. There may be more than one collector arranged to direct scattered, reflected, refracted, or transmitted light to the correct detector.

The sampling module 701 comprises, a light scattering detector 709, a fluorescence detector 709*a* and a birefringence detector 709*b*. The light scattering detector 709 is used in conjunction with the laser light source 704 to determine the scattering of light off a particle in the sensing volume 707, the fluorescence detector 709*a* is used in conjunction with the ultra-violet light source to determine the fluorescence of the particle, and the birefringence detector 709*b* is used in conjunction with the polarised light source to determine if the particle is birefringent. Note that the detectors 709, 709*a*, 709*b* may be wholly, or partially incorporated into the same detector.

The output from the detectors 709, 709*a*, 709*b* is received by a computer 720. The computer 720 also receives acquisition data 721. The acquisition data may be received by the sampling module 701, or may instead be input to the computer 720 by a user. The acquisition data 721 may relate to the direction and orientation of the light beams from the light sources 704, 704*a*, 704*b* relative to the sensing volume 707, collector 708 and/or detectors 709, 709*a*, 709*b*, for example. The acquisition data may also contain information relating to the properties of the light sources 704, 704*a*, 704*b*. The computer 720 uses the output from the one or more of sensors 709, 709*a*, 709*b* to determine properties of the particle in the sensing volume 707.

Using the output from the light scattering detector 709, the computer determines a centroid of intensity of the scattered light on a reference plane. The reference plane may coincide with a plane of the detector 709. The computer 720 then compares the position of the centroid of intensity with a radial boundary around a centre point on the reference plane corresponding to a point at which the axis of the incident laser beam intersects the reference plane. If the centroid of intensity of the scattered light is located outside the radial boundary, the computer classifies the particle as a crystalline particle.

Using the output from the fluorescence detector 709*a*, the computer measures the intensity of the fluorescent light. The computer is connected to a database 730 which stores data relating to the fluorescence of particles, such as crystalline particles. The computer 720 compares the measured intensity of the fluorescent light against data in the database 730 to determine whether the intensity of fluorescent light is within a range typically expected of crystalline particles. For example, the database may contain a value relating to the intensity of fluorescence of crystalline silica when illuminated by a particular light source having particular properties, such as a specific intensity. The acquisition data 721 may include properties of the light source 704*a*, such as its intensity. Therefore, the computer can determine whether the measured fluorescence intensity is within the range typically expected of crystalline silica particles, such as RCS.

In an alternative embodiment, the fluorescence detector 709*a* measures the spectral distribution of fluorescent light emitted by the particle, and the computer 720 compares the spectral distribution of fluorescent light of the particle with the spectral distribution of fluorescent light of known crystalline particles. The computer 720 may use a positive match, in conjunction with the determination that the centroid of intensity of the scattered light is located outside the radial boundary, to improve the reliability of the detection of crystalline particles and reduce false positives. Alternatively, a determination that the particle matches the fluorescence of a crystalline silica particle may be used on its own to determine that the particle is a crystalline silica particle.

Using the output from the birefringence detector 709*b*, the computer determines whether the particle is birefringent. The computer may also determine to what extent the particle is birefringent. If the particle exhibits birefringent properties, this information can be used on its own, or in conjunction with either or both of the measurements taken from the light scattering detector 709 and the fluorescence detector 709*a*, to determine that the particle is likely to be a crystalline silica particle.

If the computer 720 determines that the sample contains crystalline particles, such as crystalline silica particles, an estimate of particle mass concentration may be made and compared with statutory limits of exposure. If the particle mass concentration of respirable crystalline silica particles exceeds safe levels, the computer generates an output signal 711 alerting a user to the presence of the respirable crystalline particles. This may be in the form of an audio warning through one or more speakers and/or visually displayed on one or more graphical displays.

Figure 9:
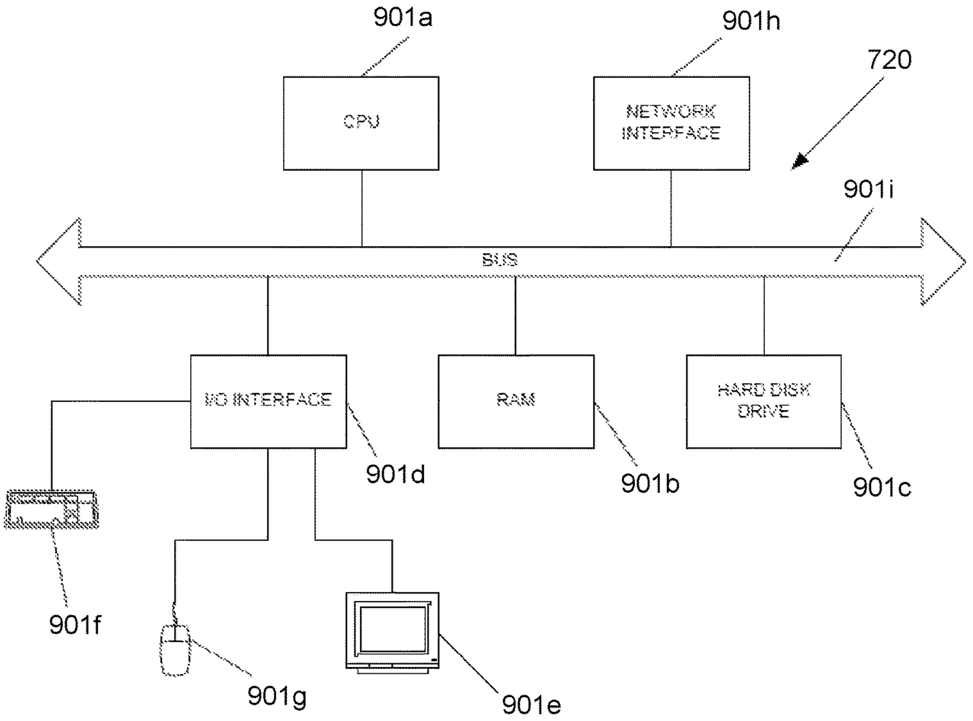
FIG. 9 is a schematic illustration of a device suitable for use in the apparatus of FIGS. 6 to 8.

FIG. 9 shows the computer 720 in further detail. It can be seen that the computer comprises a CPU 901*a* which is configured to read and execute instructions stored in a volatile memory 901*b* which takes the form of a random access memory. The volatile memory 901*b* stores instructions for execution by the CPU 901*a* and data used by those instructions. For example, in use, data such as data received from the detectors 709, 709*a*, 709*b* may be stored in volatile memory 901*b*.

The computer 720 further comprises non-volatile storage in the form of a hard disc drive 901*c*. It will be appreciated by the skilled person that any non-volatile storage may be used, such as a solid state drive. Data such as data received from any of detectors 709, 709*a*, 709*b* may be stored on hard disc drive 901*c* and may for example be analysed to generate an output signal 711. The computer 720 further comprises an I/O interface 901*d* to which are connected peripheral devices used in connection with the computer 720. More particularly, a display 901*e* is configured so as to display output from the computer 720 such as output 711 in the form of a warning indication such as an indication of a risk level associated with the detection of RCS. The computer may also comprise one or more speakers (not shown) which can be used to provide an audio alert. Input devices are also connected to the I/O interface 901*d*. Such input devices may include a keyboard 901*f* and a mouse 901*g* which allow user interaction with the computer 720. It will be appreciated that the computer may have other input interfaces, for example a touch screen. A network interface 901*h* allows the computer 720 to be connected to an appropriate communications network so as to receive and transmit data from and to other computers. The input devices can be used such that the computer is able to receive the data captured by any one of the detectors and/or the acquisition data. The CPU 901*a*, volatile memory 901*b*, hard disc drive 901*c*, I/O interface 901*d*, and network interface 901*h*, are connected together by a bus 901*i*. It will be appreciated that the foregoing description of the computer 720 is an example computer set up suitable for carrying out aspects of the invention, and the skilled person will recognise that various modifications may be made to the computer 720.

Any suitable optical detector may be used. For example, the detector could be an imaging device, such as a CMOS or CCD detector array or a multi-segment photodiode, capable of recording the pattern of scattered light from the particle.

In some embodiments it may be necessary to record the individual light scattering patterns from many thousands of particles per second. Reading out the recorded data from optical detectors that comprise many discrete optical sensors or 'pixels' may be too slow for use in a real-time particle analysis apparatus such as the one described herein. Such devices can also require complex and often expensive electronics to acquire and render the recorded data in a useable format.

A PSD (as described above with reference to FIG. 6) is fabricated as a single photosensitive element but, by virtue of electrical voltages applied laterally across the device, is able to generate currents within the device that are related to the distribution of light falling onto the device. By simple measurement of the magnitudes of orthogonal currents flowing through the device it is possible to accurately determine the centroid of intensity of the light distribution falling on the device.

The use of PSD devices in the analysis of two-dimensional light scattering patterns has significant advantages over other technologies (such as CMOS or CCD arrays) in terms of lower cost and speed of response. In terms of the latter property, the data from PSD devices can be read out in typically the order of 1 to 2 microseconds, whereas CMOS or CCD arrays would typically require millisecond read-out times.

PSD devices record the magnitudes of two currents produced when a pattern of scattered light falls onto the PSD. The magnitude of these two currents is related via a simple and well-known equation to the x-y coordinates on the PSD of the centroid of intensity of the light scattering pattern. This equation can be executed by a microprocessor in an external device such as a computer, or a small low-cost electronic microprocessor contained within the PSD.

The sum of the currents generated by the light falling onto the PSD is also related, via light scattering theory, to the size of the scattering particle. Therefore, information relating to the sum of the currents may be used to determine the particle size, which can then be used to assist with assessing the mass of the particle, and whether the particle is respirable. For example, the PSD 609 may detect scattered light from a particle with the centroid of intensity significantly offset from the central axis. However, the sum of the currents may indicate that the particle is too large to be respirable (for example, may be greater than about 20 μm) and therefore can be disregarded by the apparatus in its determination of the concentration of RCS.

Figure 10:
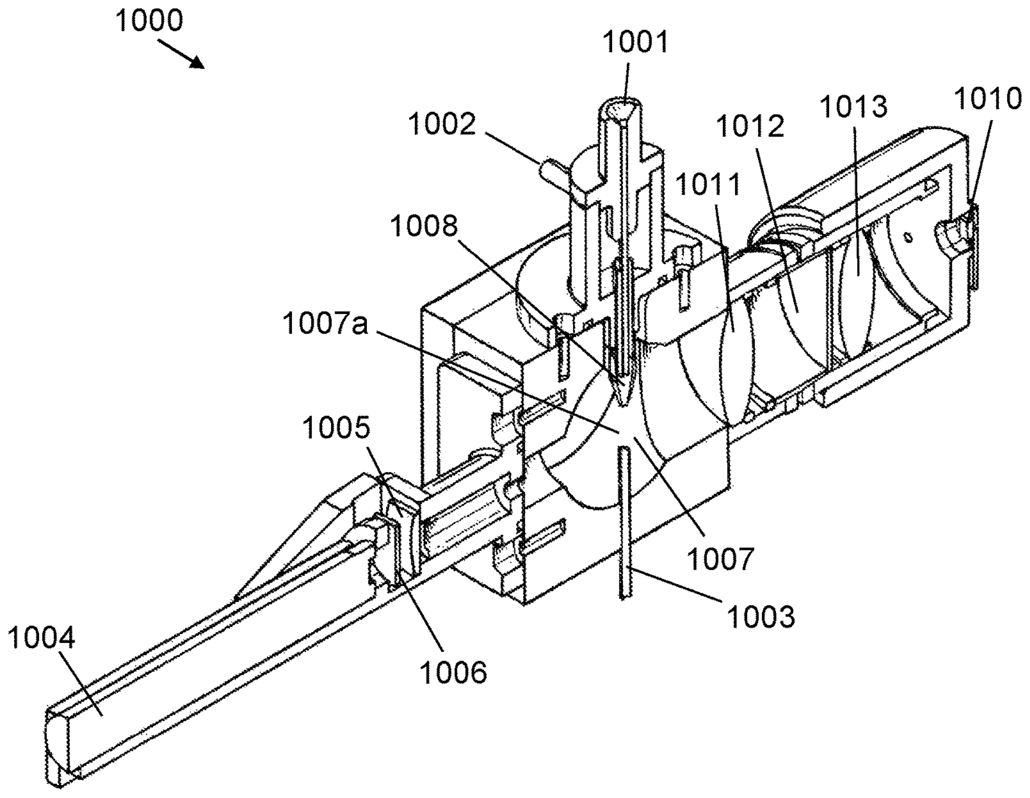
FIG. 10 illustrates a cross section of a detection apparatus according to an embodiment.
Figure 11:
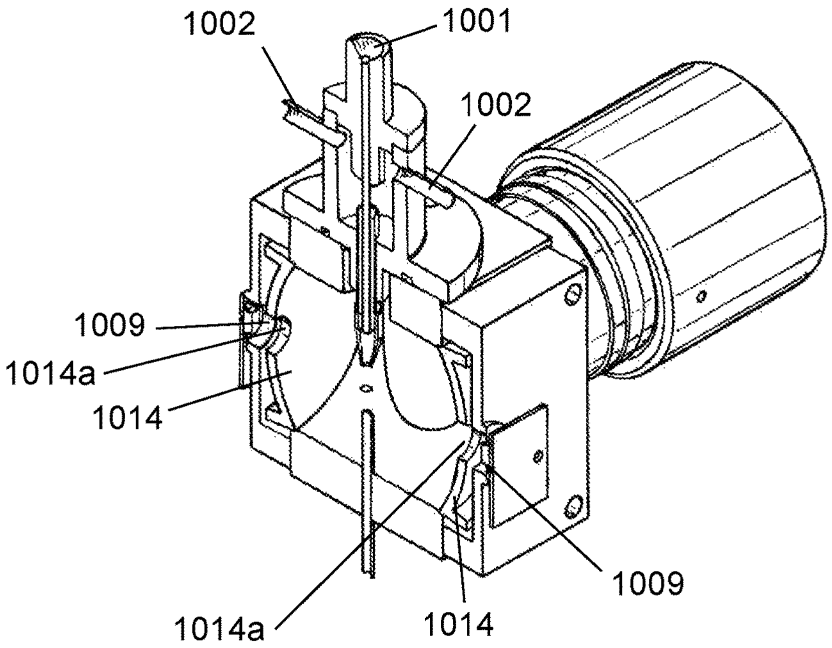
FIG. 11 illustrates a second cross section of the detection apparatus of FIG. 10.

FIG. 10 shows an apparatus 1000, through a first cross section, for detecting crystalline particles, such as RCS, according to an alternative embodiment. FIG. 11 shows the apparatus 1000, through a second cross section. Ambient airborne particles, which may or may not contain crystalline particles, are drawn by an air pump (not shown) into the apparatus 1000 through a sample delivery tube 1001. The air pump may alternatively comprise any suitable means that allows air to move through the apparatus 1000, such as a fan. To ensure the particles in a sample airflow are constrained when passing through the apparatus 1000, a sheath-flow (not shown) of filtered clean air may be added via one or more sheath-flow ports 1002 to surround the particle flow. As described above, a sheath flow helps to prevent particles at the edges of the flow being drawn out of the flow and into the chamber where they can contaminate, and over time, degrade the optical surfaces. The combined sample airflow and sheath flow leave the instrument through a vent tube 1003. The combined sample and sheath flows may be aerodynamically configured to ensure that particles contained within the sample flow are essentially travelling in single file in the direction of flow. The apparatus 1000 may comprise one or more High-efficiency Particulate Arrestance (HEPA) particle filters (not shown), which can be used to filter the sheath flow and can also be used to protect an air pump from particulate contamination, for example. The skilled person will of course recognise that there are other ways to configure the sample flow such that the particles contained within the sample flow travel in single file, where some of these ways do not require a sheath flow.

The apparatus 1000 comprises a diode laser module 1004. In an embodiment, the diode laser module 1004 produces a laser beam having a wavelength between (and including) 680 and 510 nm. The apparatus 1000 further comprises a first polarizer 1006 arranged to polarize the laser beam light in a first direction. The apparatus 1000 further comprises a cylindrical lens 1005. The diode laser module 1004, first polarizer 1006 and cylindrical lens 1005 are configured to produce a parallel beam of polarized light. The parallel beam of polarized light may be elliptical in cross-section. The parallel beam of polarized light is configured to intersect the sample airflow within a scattering chamber 1007, where the point of intersection defines a sensing volume 1007*a* in which the parallel beam of polarized light intersects particles in the sample airflow. A tapered delivery nozzle 1008 may be used to help direct the sample airflow within a scattering chamber 1007.

The apparatus 1000 comprises three light detectors configured to detect the presence of light. Two of the light detectors are scatter detectors 1009 (see FIG. 11) and one of the light detectors is a birefringence detector 1010.

The birefringence detector 1010 is arranged along the laser beam axis, such that in the absence of any airborne particles, the laser beam intersects a detector surface of the birefringence detector 1010.

Located between the scattering chamber 1007 and the birefringence detector 1010 is a first collimating lens 1011, second polarizer 1012 and second collimating lens 1013. The first and second collimating lenses 1011, 1013 are configured to direct light passing through the lenses 1011, 1013 to the birefringence detector 1010. It will be appreciated that, in some embodiments, there may be greater or fewer collimating lenses, including none.

The second polarizer 1012 is a polarizer which polarizes the light in a second direction which is opposite to the first direction of the first polarizer. For example, the first polarizer may be a right hand polarizer and the second polarizer may be a left hand polarizer. The configuration of the first and second polarizers 1006, 1012 having opposite polarisations ensure that light passing through the first polarizer 1006 cannot pass through the second polarizer 1012, unless the polarisation of the light is further modified between the first and second polarizers 1006, 1012. Therefore, in the absence of birefringent particles, the polarised laser beam, having passed through the first polarizer 1006, will be incident on, but will not be transmitted through the second polarizer 1012 such that the laser beam will not reach the birefringent detector 1010. However, if the polarised laser beam is incident on, and refracted through, a birefringent particle, such as a crystalline silica particle, a component of the laser beam's polarisation will be modified as it is refracted though the birefringent particle. As such, the modified polarized laser beam will be transmitted through the second polarizer 1012 and incident on the birefringence detector 1010, where the birefringence detector 1010 will register a detection of light. Detection of light incident on the birefringence detector 1010 causes an output to be generated indicating that a particle is birefringent and may additionally indicate a magnitude of the detected light signal such that the strength of the birefringence signal may be determined.

It will be appreciated that a small amount of light will typically reach the birefringence detector 1010 in the absence of birefringent particles. However the ratio of light incident on the birefringence detector 1010 to that transmitted is typically greater than 6000:1. As such, in some embodiments a threshold value may be used to provide a lower limit of light required to be incident on the birefringence detector 1010 for a particle to be determined to be birefringent.

In order to determine that an air sample contains birefringent particles, such as RCS, the determination may be based over a period of time, or over a specific number of particles passing through the apparatus. For example, an air sample may be monitored over a period of time, and it may be determined that the air sample contains birefringent particles only if there are greater than a threshold of light detections recorded at the birefringence detector. Alternatively or additionally, the magnitude of the detected light signal may be taken into account when determining the presence of birefringent particles.

Figure 12A:
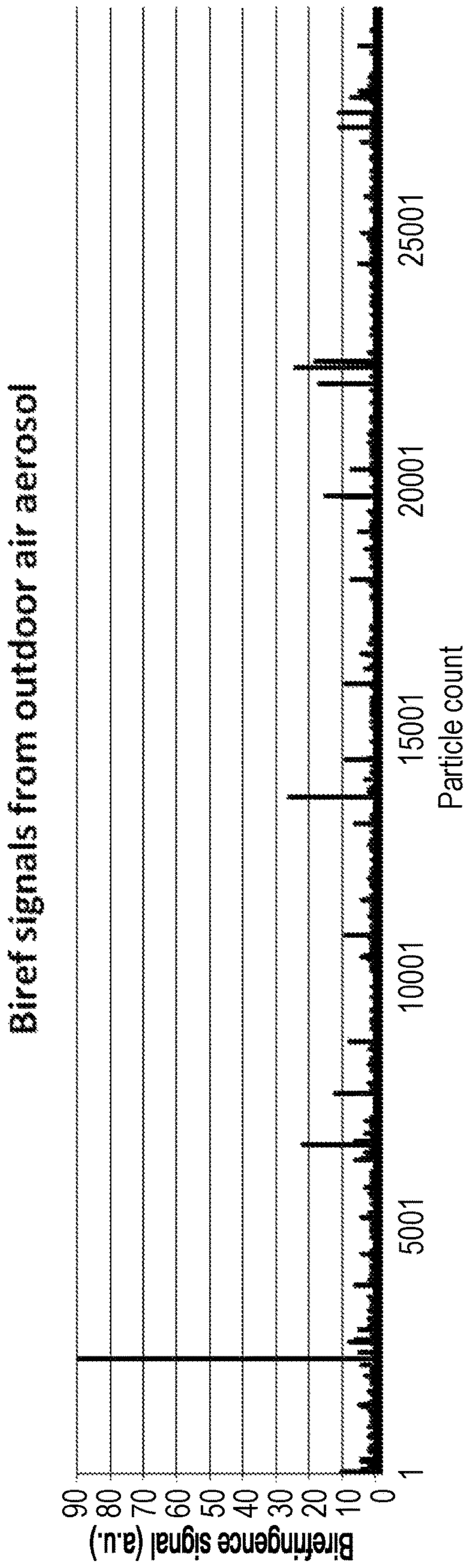
FIG. 12A is a plot of birefringence measurements from an aerosol that does not contain RCS.
Figure 12B:
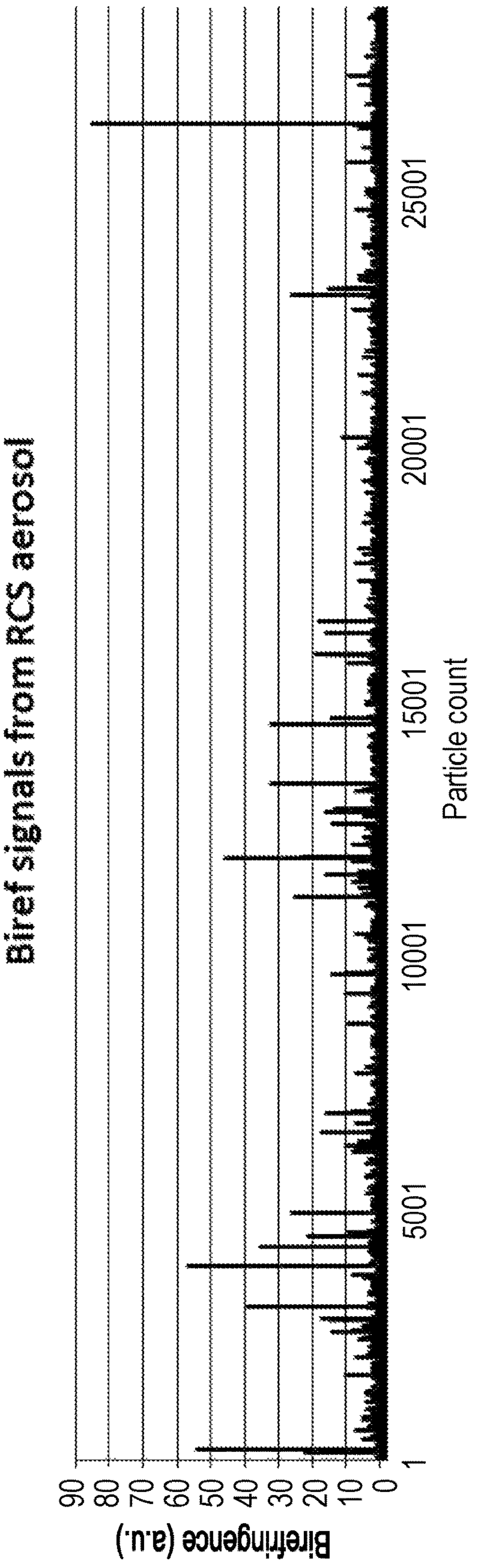
FIG. 12B is a plot of birefringence measurements from an RCS aerosol.

FIGS. 12A and 12B each show a plot of birefringence signals for approximately twenty five thousand particles obtained using a device comprising a birefringence detector as described above. In each of FIGS. 12A and 12B, the x-axis indicates individual particles detected in the detector, and the y-axis indicates the relative response of the detector for each particle (measured in arbitrary units). FIG. 12A shows a plot of particles in an outdoor air aerosol that does not include RCS particles and FIG. 12B shows a plot of particles in an outdoor air aerosol that is known to include RCS particles. Statistical analysis of the data samples can be performed to determine values for an indication that a particle is birefringent and/or a threshold value for determining that an air sample contains RCS particles. For example, it can be seen that there is a measurable increase in both the frequency of high birefringence values and also the mean magnitude of birefringence across all particles in FIG. 12B when compared with FIG. 12A.

The apparatus 1000 further comprises two elliptical scatter collection mirrors 1014 which are located at either side of the laser beam and are configured to oppose one another (shown in FIG. 11). The two elliptical scatter collection mirrors 1014 are each arranged to collect light scattered from a particle in respective directions and direct the scattered light onto one of the scatter detectors 1009. In an embodiment, the elliptical scatter collection mirrors 1014 are configured to collect light scattered at an angle of between 30 degrees and 150 degrees from an axis of the laser beam, and in a more preferred embodiment, between 60 degrees and 120 degrees.

In the example shown, each scatter detector 1009 is located behind a corresponding scatter collection mirror 1014, where each scatter collection mirror 1014 comprises an aperture 1014*a* in its centre through which light directed off the opposing scatter collection mirror 1014 may pass to reach the scatter detector 1009.

Due to the arrangement of the elliptical scatter collection mirrors 1014 being off the axis of the laser beam, light will only be collected at one of the collection mirrors in the event that light incident on the particle is scattered by the particle. In the event that the laser beam is incident on crystalline particles, such as RCS, the light will generally be scattered asymmetrically (as described above). This behaviour is in contrast to the generally symmetrical scattering of light by non-crystalline particles (see FIG. 1).

Therefore, by placing two elliptical scatter collection mirrors 1014 either side of the laser beam, a detection of more light in one of the scatter detectors 1009 than the other indicates that the light has been scattered by a particle in an asymmetrical manner.

The apparatus 1000 may be configured to determine a ratio between the light detected at one of the scatter detectors 1009 relative to the light detected at the other of the scatter detectors 1009. A scattering ratio threshold may be set such that if a scattering ratio is measured above the threshold, it is determined that a particle which produced the scattering ratio is a crystalline particle. An example ratio may be equal to or greater than 3:1. Alternatively, a suitable ratio may be determined based upon empirical analysis of light scattering in a particular environment.

In order to determine that an air sample contains crystalline particles, such as RCS, the determination may be based over a period of time, or over a specific number of particles passing through the apparatus. For example, an air sample may be monitored over a period of time, and it may be determined that the air sample contains crystalline particles only if the threshold scattering ratio is exceeded for a particular number of times over that period of time.

Figure 13A:
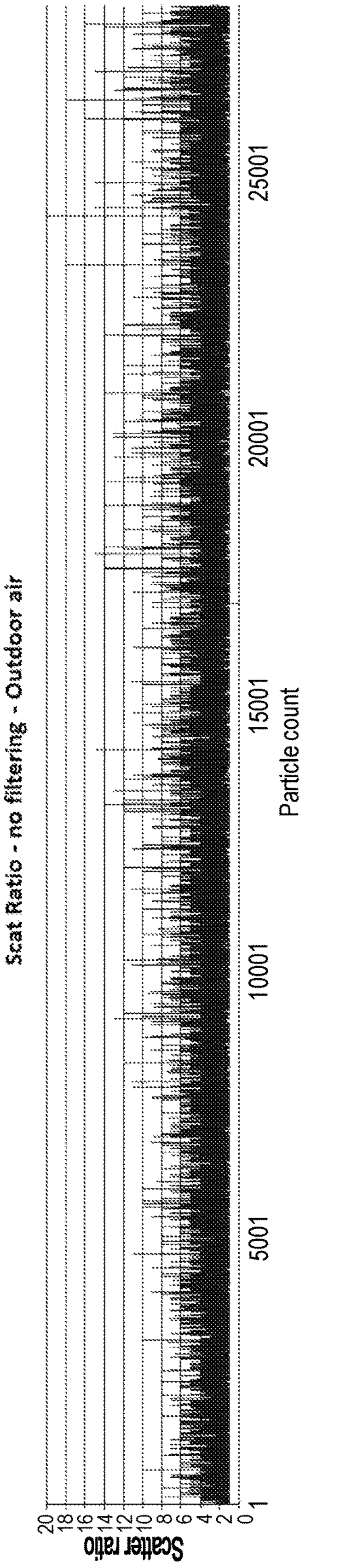
FIG. 13A is a plot of scattering ratio measurements from an aerosol that does not containing RCS.
Figure 13B:
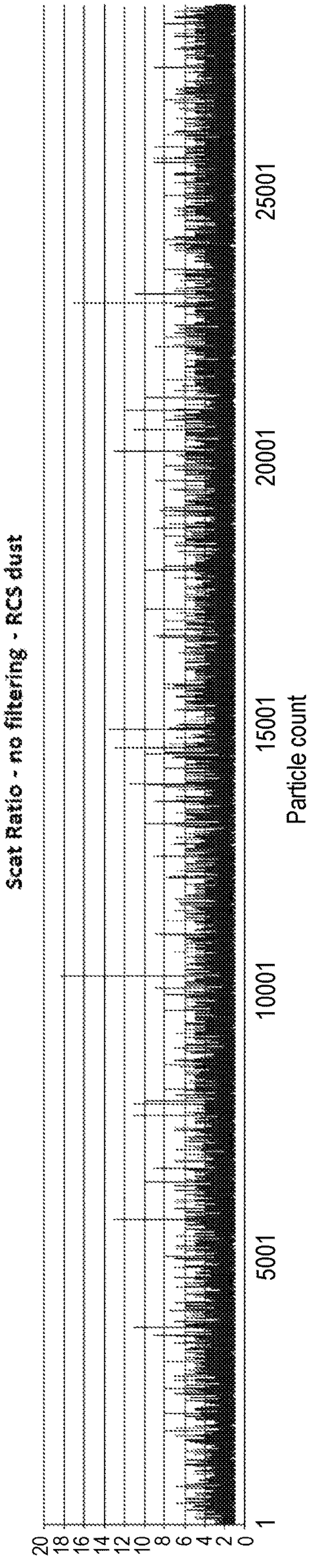
FIG. 13B is a plot of scattering ratio measurements from an RCS aerosol.

FIGS. 13A and 13B each show a plot of particle scatter ratio signals for approximately twenty five thousand particles obtained using a device comprising two scatter detectors 1009 as described above. In each of FIGS. 13A and 13B, the x-axis indicates individual particles detected in the detector, and the y-axis indicates the scatter ratio recorded for each particle. FIG. 13A shows a plot of particles in an outdoor air aerosol that does not include RCS particles and FIG. 13B shows a plot of particles in an outdoor air aerosol that is known to include RCS particles. Statistical analysis of the data samples can be performed to determine values for an indication that a particle is a crystalline particle, such as RCS, and/or a threshold value for determining that an air sample contains RCS particles.

Figure 14A:
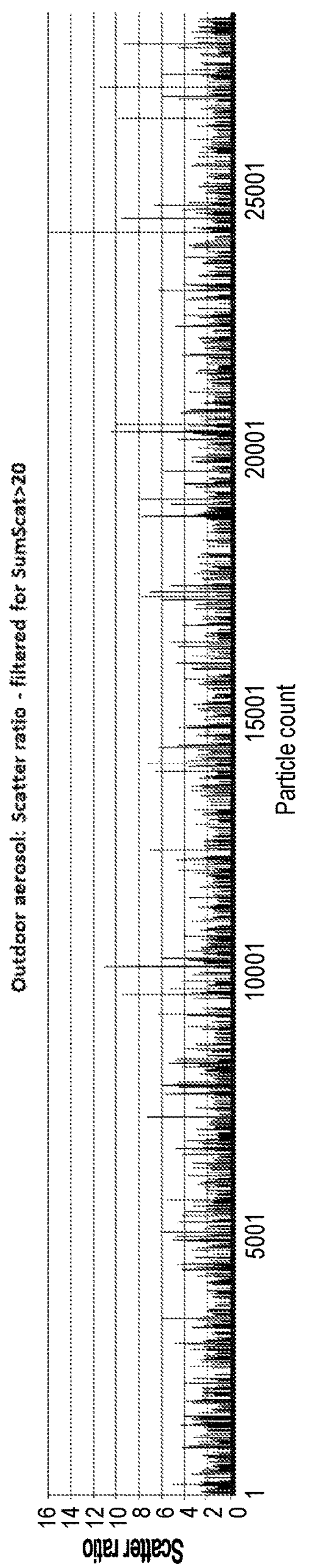
FIG. 14A is a plot of scattering ratio measurements from an aerosol that does not containing RCS when filtering is applied.
Figure 14B:
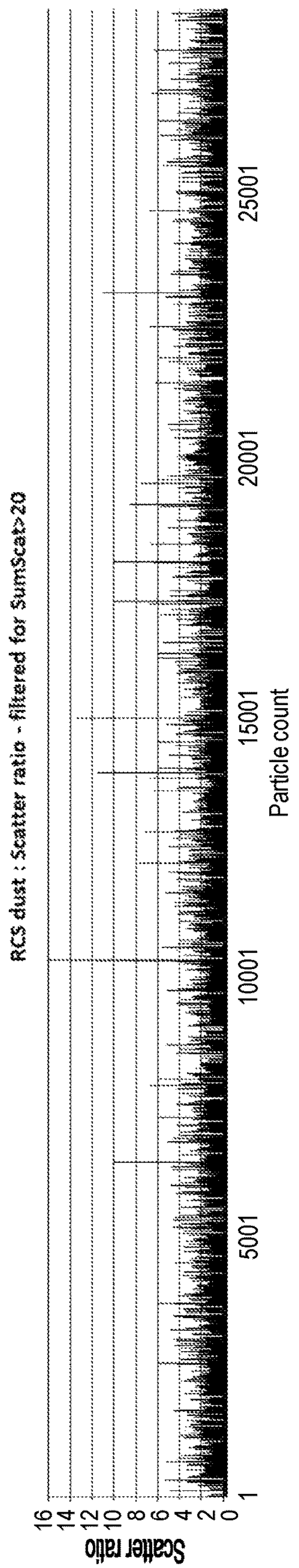
FIG. 14B is a plot of scattering ratio measurements from an RCS aerosol when filtering is applied.

In some embodiments filtering may be applied to the data obtained from the scatter detectors 1009. For example, particles for which the sum of the output of both scatter detectors 1009 is less than a predetermined threshold may be removed from consideration. Particles for which the sum of the output of both scatter detectors 1009 are typically relatively small particles and those particles may be removed from consideration. In particular, it has been found that the ratio between light detected at the two scatter detectors 1009 for relatively small particles is typically artificially high due to signal to noise effects. A suitable threshold value for filtering may be empirically determined based upon a sample in an environment. For example, a threshold value may be selected to remove the smallest 5% of particles or the smallest 10% of particles or any other suitable percentage of particles. FIGS. 14A and 14B illustrate the data of FIGS. 13A and 13B after filtering has been applied by setting the ratio for removed particles equal to zero. It can be seen that the filtering applied to the data results in more readily identified differences between the two data sets and may provide improved detection of crystalline particles in the environment.

The apparatus 1000 may determine that an air sample contains RCS based on both measurements from the scatter detectors 1009 and the birefringence detector 1010. Whether an RCS particle, when illuminated, produces a detectable scattering pattern or detectable birefringence is determined by the RCS particle's shape and orientation during illumination. For example, if an RCS particle is orientated such that it produces an asymmetrical scattering pattern, it will typically produce a relatively weak birefringence detection, as much of the laser light will have been reflected by the particle rather than refracted through the particle to the birefringence detector 1010. Similarly, if the shape and orientation of the RCS particle is such so as to give rise to optimal birefringence, the particle will typically produce a sub-optimal scattering pattern. Therefore, it can be difficult to detect both an asymmetrical scatter pattern and birefringence from the same particle.

The apparatus 1000 may therefore be configured to analyse measurements obtained by detectors 1009, 1010 over a given time period, or over a given number of particles passing through the apparatus. For example, the apparatus 1000 may determine the number of times in a time period that the scattering ratio threshold is exceeded, and correlate this with the number of times a measure of birefringence is detected in the same time period. If, during the time period, there is an observed increase in the measure of asymmetrical scattering when compared with a background, as well as an observed increase in the measure of birefringent detections when compared with a background, then it may be determined that the air sample passing through the apparatus 1000 during the time period contains crystalline silica, such as RCS. A statistical analysis may be carried out on the recorded detections over the time period and compared with a background reading to determine a likelihood that the air sample contains RCS. For example, the determination that an air sample contains RCS, based on recorded measurements over a given time period, may be determined to a 99% confidence level.

If, during the time period or for a predetermined number of particles, there is an observed increase in the measure of asymmetrical scattering, but there is no observed increase in the measure of birefringence, it may be determined that crystalline silica is not present in the air sample. Similarly, if, during the time period or for a predetermined number of particles, there is an observed increase in the measure of birefringence, but there is no observed increase in the measure asymmetric scattering, it may also be determined that crystalline silica is not present in the air sample.

The apparatus 1000 may use recorded data from previous time periods to assist with determining whether an air sample contains crystalline silica, such as RCS. For example, if during a first time period, RCS is determined to be present at a 99% confidence level, and at a second time period, RCS is also determined to be present at a 99% confidence level, then the apparatus 1000 may combine this prior knowledge to generate updated likelihoods that the air sample contains RCS.

While it has been described that RCS is determined based on measuring birefringence and scattering of particles, it will be appreciated that the determination of RCS in a sample may be based on either a measurement of birefringence or scatter properties. For example, a measure of an unusually high concentration of birefringent particles in a region that is likely to contain RCS, such as a fracking site, may provide a sufficient indication that an air sample contains RCS. As such, in some embodiments the apparatus 1000 may be provided without scatter detectors 1009. Similarly, in some embodiments the apparatus 1000 may be provided without a birefringence detector 1010.

In an embodiment, the first and second polarizers 1006, 1012 are circular polarizers. For example, the first polarizer 1006 may be arranged such that left hand circularly polarized light is transmitted from the first polarizer 1006, and the second polarizer 1012 may be arranged such that right hand circularly polarized light is transmitted from the second polarizer 1012. Using circularly polarized light instead of linear polarized light can lead to better performance in detecting birefringence. A circular polarizer may be formed from a combination of a first linear polarizing element and a quarter-wave plate configured to have an orientation at 45° to the axis of the first linear polarizing element. In an example configuration, a linearly polarized laser beam may be arranged with its polarization parallel to the first linear polarizing element for maximum transmission through the first linear polarizing element. The linearly polarized light may then be transmitted though the quarter-wave plate such that light that passes into the scattering chamber 1007 is either right-hand circularly polarized, or left-hand circularly polarized, depending on the configuration of the polarizer.

Combining use of a laser which outputs a laser beam having a wavelength of 520 nm, with circular polarizing elements has been found to provide improved performance in detecting birefringence with reduced noise over using lasers having greater wavelengths. For example, it has been found that the proportion of particles in a sample containing RCS giving a relatively high value of birefringence is increased, typically by a factor of 2 to 3, when using the combination of a laser which outputs a laser beam having a wavelength of 520 nm and circular polarizers. Whilst a laser beam having a wavelength of 520 nm has been found to be advantageous, it will be appreciated that laser beams having a similar wavelength, for example in the range 500 nm to 540 nm can be used.

Figure 15A:
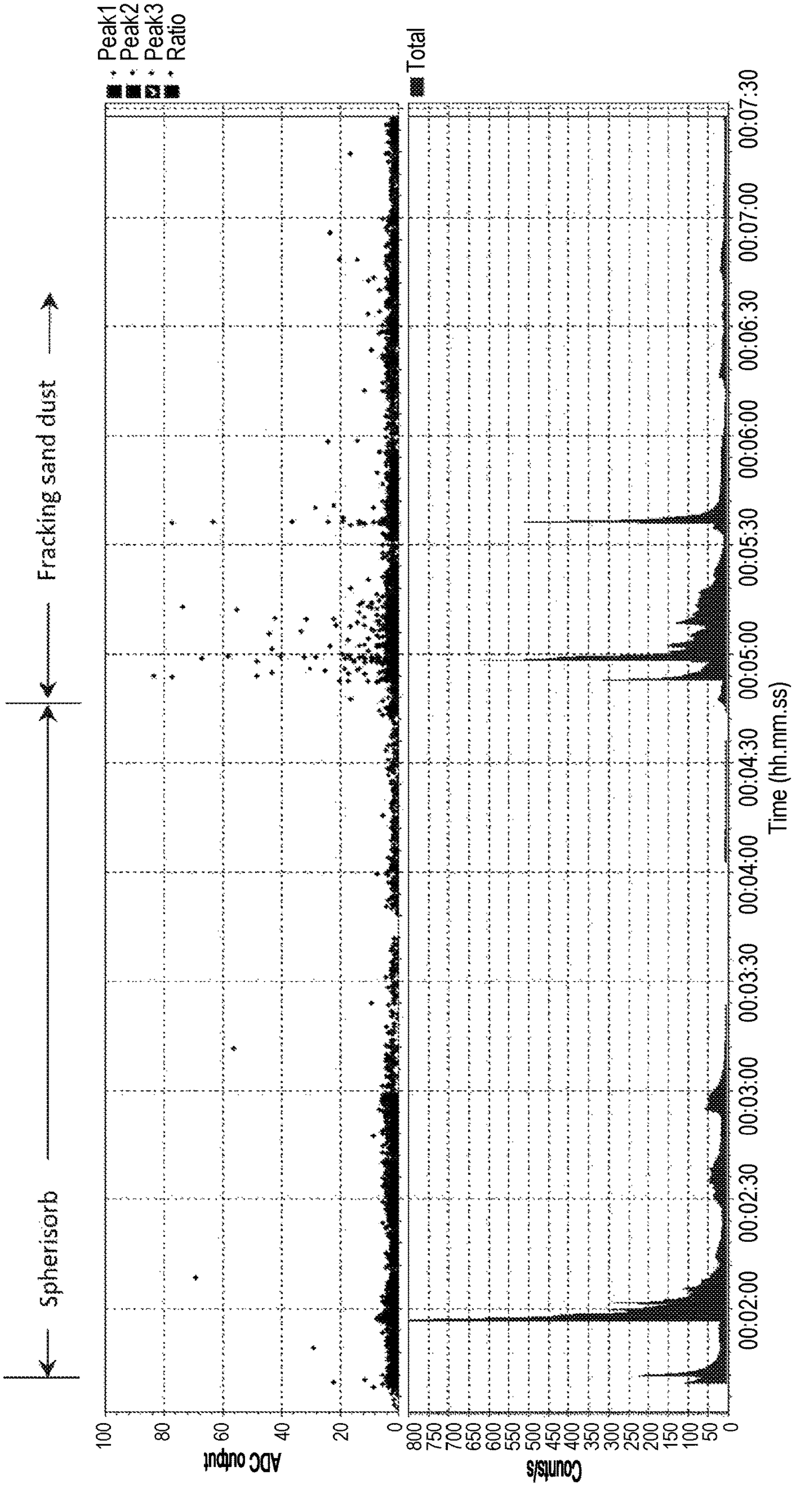
FIG. 15A is a plot of birefringence and particle count measurements over a period of time for a crystalline silica and non-crystalline silica.

FIG. 15A shows a plot of birefringence signals measured from an aerosol containing non-crystalline silica (such as Spherisorb®) and an aerosol containing crystalline silica (such as fracking sand dust) when using the apparatus 1000, where the laser 1004 outputs a laser beam having a wavelength of 520 nm, and the first and second polarizing elements 1006, 1012 are circular polarizing elements. The x-axis indicates time elapsed, and the y-axis of the upper part of the plot indicates birefringence signal magnitudes in terms of A/D converter output (bits), and the y-axis of the lower part of the plot indicates a number of particles detected in a given time period.

The non-crystalline silica aerosol was tested first by being released in several bursts over a period of approximately 4 minutes. The particle count-rate (lower trace) recorded by the apparatus during this time reached high levels, approaching 800 particles/second. However, the birefringence signals recorded (upper trace) exhibited very few particles with a birefringence signal greater than 6. The fracking sand dust aerosol was then tested by being released in several bursts over a period of several minutes (starting at around 4 minutes 50 seconds). As can be seen the fracking sand dust aerosol, although producing slightly lower count rates, resulted in a higher proportion of birefringence signals greater than 6, and, while not shown, some birefringence signals exceeded 100 in magnitude.

Since the two aerosolised materials were both essentially the same material, silica, with the difference being that non-crystalline silica is amorphous and fracking sand dust is crystalline, the result in FIG. 15A demonstrates the ability of the apparatus 1000 to differentiate crystalline silica from non-crystalline silica particles using only birefringence. However, the data could be combined with light scattering data, as described above, to further improve the confidence in detecting crystalline silica.

Figure 15B:
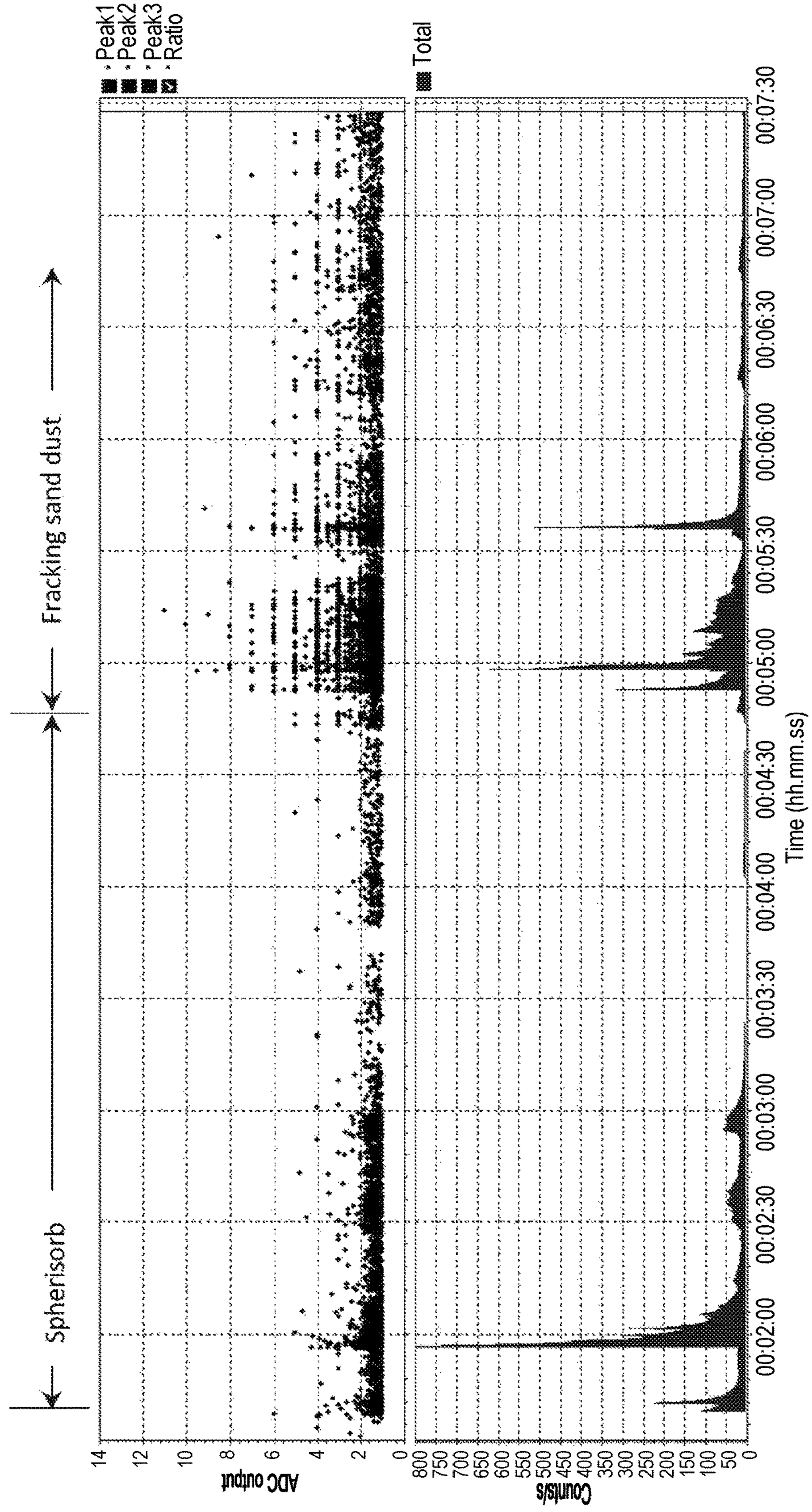
FIG. 15B is a plot of scattering ratio and particle count measurements over a period of time for a crystalline silica and non-crystalline silica.

FIG. 15B is arranged in a similar manner to FIG. 15A, but shows the recorded measurements of the scatter ratio data from the two aerosols over the same time period as in FIG. 15A. As can be seen in the upper trace, the fracking sand dust aerosol produces significantly higher scatter ratio values than the non-crystalline silica aerosol. This further demonstrates the ability of the apparatus 1000 to differentiate crystalline silica from other non-crystalline airborne particle types using scattering data.

The output data recorded by the birefringence and scatter detectors 1009, 1010, may be processed by an application or computer program for displaying real time values of RCS data. In some configurations, the application or computer program may interrogate the apparatus 1000 at specific time intervals, such as every 30 seconds, and then record and/or display on a monitor relevant data, such as the RCS particle concentration over the last time interval, for example. In some embodiments, if crystalline particles are detected, an estimate of particle mass concentration may be made and compared with statutory limits of exposure. If the particle mass concentration of the crystalline particles exceeds safe levels, personal working in an area where crystalline particles are detected may be warned. Particle mass may, for example, be determined based upon a sum of light scattering values detected at the two light scattering detectors.

In an example configuration, the sample flowrate through the scattering chamber may be between 400 and 500 ml/min. The sheath flow may be between 1000 and 1100 ml/min. In an exemplary configuration, the sheath flow may be 1,010 ml/min and the sample flowrate may be 461 ml/min, giving a total flowrate of 1,471 ml/min.

The apparatus 1000 may comprise a storage device for storing data recorded by the birefringence detector 1010 and the scatter detectors 1009. The storage device may be non-volatile or volatile. The storage device may be a removable storage device, such as a flash drive, SD card or SIM card.

The scatter detectors 1009 and birefringence detector 1010 may be any type of light detector. For example, the scatter detectors 1009 and birefringence detector 1010 could be an imaging device, such as a CMOS or CCD detector array or a multi-segment photodiode, capable of recording light.

While two scatter detectors 1009 have been described, it will be appreciated that any suitable number of scatter detectors 1009 may be used.

Any of the embodiments and examples described above may be combined where appropriate. For example, the apparatus 1000 may comprise, or be connected to, the computer 720 described above, or the apparatus 700 may comprise the "green" laser and/or circular polarizers.

While it has been described that a determination that a crystalline particle is respirable is based upon determining a particles size via light scattering theory, the skilled person will recognise that the size need not be calculated, but may be assumed. For example, if the apparatus described herein is used in an environment where it is known that there are crystalline particles being used that are of a respirable size, then it may not be necessary to calculate each particle's size.

Although specific embodiments of the invention have been described above, it will be appreciated that various modifications can be made to the described embodiments without departing from the spirit and scope of the present invention. That is, the described embodiments are to be considered in all respects exemplary and non-limiting. In particular, where a particular form has been described for particular processing, it will be appreciated that such processing may be carried out in any suitable form arranged to provide suitable output data.

The invention claimed is:

1. A method for determining the presence of crystalline silica particles in a sample comprising a plurality of particles, the method comprising:

receiving first data generated based upon light scattered by at least one particle of said plurality of particles, wherein said first data is based upon a difference between light scattered by said at least one particle in first and second directions, the first data being indicative of asymmetric scattering by the at least one particle;

receiving second data generated based upon light transmitted through at least one particle of said plurality of particles, the second data being indicative of birefringence of the at least one particle; and determining the presence of crystalline silica particles in the sample based upon the first data and second data.

2. A method according to claim 1, wherein said first data is based upon a first output of a first detector associated with said first direction and a second output of a second detector associated with said second direction.

3. A method according to claim 2, wherein said first detector is arranged to detect light scattered by said particle on a first side of a plane defined based upon a source of said light and said particle and said second detector is arranged to detect light scattered by said particle on a second side of said plane.

4. A method according to claim 1, further comprising, for each particle of said plurality of particles associated with said first data:

determining whether said light scattered by said particle in first and second directions satisfies a predetermined criterion; and determining the presence of crystalline silica particles in the sample based upon light scattered by said particle if said predetermined criterion is satisfied.

5. A method according to claim 4, wherein said predetermined criterion is based upon a total light scattered in said first and second direction.

6. A method according to claim 1, wherein said first data is based upon third output of a third detector and data indicating a relationship between the third detector and the light source.

7. A method according to claim 1, wherein said second data is based upon a change in polarity of said light transmitted through said at least one particle.

8. A method according to claim 7, further comprising:

emitting, from a light source, a polarized light beam, wherein said light transmitted through said at least one particle is light of said polarized light beam incident on said particle.

9. A method according to claim 1, further comprising receiving first reference data associated with said at least one of said first and second data, wherein said determining is further based upon said first reference data and determining a difference between said first reference data and said at least one of said first and second data associated with said first reference data.

10. A method according to claim 9, wherein said first reference data is based upon data generated from measurements of a background sample comprising a plurality of particles.

11. A device for detecting the presence of a crystalline silica particle in a gas sample, the device comprising:

a polarised light source arranged to emit a light beam having a first polarisation onto a particle of said gas sample;

a detector arranged to detect light transmitted through said particle having a polarisation different to said first polarisation;

a further detector arranged to detect light scattered asymmetrically by the particle when the light beam is incident on the particle, wherein the further detector comprises a first detector arranged to detect light scattered by the particle in a first direction and a second detector arranged to detect light scattered by the particle in a second direction; and a processor arranged to determine the presence of a crystalline silica particle in the gas based upon output of said detector, and said further detector.

12. A device according to claim 11, further comprising a second polariser, wherein said second polariser is arranged such that light detected at said detector is transmitted through said second polariser, and wherein said second polariser is arranged to prevent light having said first polarisation being transmitted to said detector.

13. A device according to claim 11, wherein said processor is arranged to process said output of said detector based upon a threshold.

14. A device according to claim 11, wherein said processor is arranged to receive output of said detector associated with a plurality of particles, wherein determining the presence of a crystalline silica particle in the gas is based upon said output of said detector associated with said plurality of particles.

15. A device according to claim 14, wherein said processor is arranged to determine a relationship between said output of said detector associated with said plurality of particles and reference data.

16. A device according to claim 11, further comprising:

an inlet; and a detection chamber;

wherein said detection chamber is arranged to receive a particle in the gas sample whilst light is emitted onto the particle.

* * * * *